United States Patent [19]

Wu

[11] Patent Number: 5,648,484

[45] Date of Patent: Jul. 15, 1997

[54] CATALYTIC ENANTIOSELECTIVE SYNTHESIS OF A SPRIOFUSED AZETIDINONE

[75] Inventor: Guang-Zhong Wu, Somerville, N.J.

[73] Assignee: Schering Corporation, Kenilworth, N.J.

[21] Appl. No.: 451,111

[22] Filed: May 25, 1995

Related U.S. Application Data

[63] Continuation of Ser. No. 399,859, Mar. 7, 1995, abandoned.
[51] Int. Cl.$^6$ ............... C07D 205/12; C07D 317/72; C07D 319/08; C07F 7/18
[52] U.S. Cl. ............ 540/203; 540/214; 540/342; 540/333
[58] Field of Search ............... 540/203; 549/342, 549/333

[56] References Cited

U.S. PATENT DOCUMENTS 4,692,515  9/1987  Georgiev ................... 540/203

FOREIGN PATENT DOCUMENTS

WO94/17038  8/1994  WIPO .

OTHER PUBLICATIONS

Fieser, "Organic Chemistry, Second Edition" (1950) pp. 431–432.

Parmee et al., J. Am. Chem. Soc. 1991, 113,9365–9366.

Kiyooka et al., J. Org. Chem. 1991, 56, 2276–2278.

Sanchez et al., Synthetic Communications, 15(2), 141–149 (1985).

Basha et al., Tetrahedron Letters, No. 48, pp. 4171–4173 (1974).

Mikami et al., J. Am. Chem. Soc. 1989, 111, 1940–1941.

Kiyooka et al., Tetrahedron Letters, vol. 33, No. 34, pp. 4927–4930 (1992).

Corey et al., J. Am. Chem. Soc. 1991, 113, pp. 8966–8967 (plus supplementary material).

Shirai, Tet. Letters 29, 6461 (1988).

"Concise Encyclopedia Chemistry" (1994), p. 59.

*Primary Examiner*—Mark L. Berch
*Attorney, Agent, or Firm*—Henry C. Jeanette; Anita W. Magatti

[57] ABSTRACT

A process for producing a compound of the formula

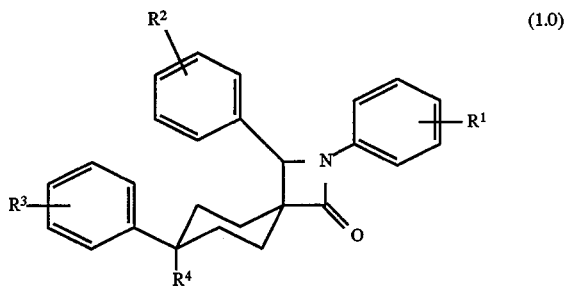

comprises the following sequence of steps:

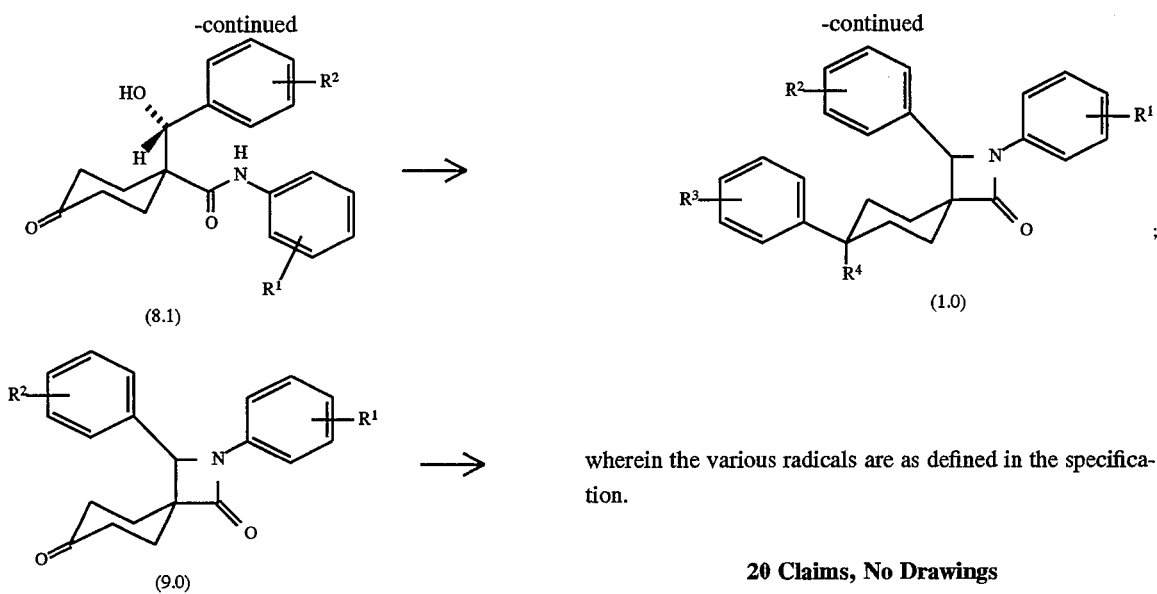
wherein the various radicals are as defined in the specification.
20 Claims, No Drawings

CATALYTIC ENANTIOSELECTIVE SYNTHESIS OF A SPRIOFUSED AZETIDINONE

This is a continuation of application Ser. No. 08/399859, filed Mar. 7, 1995 abandoned.

BACKGROUND

Asymmetric spiro-fused azetidinones are useful pharmaceutical compounds. Thus, any efficient process for producing these compounds in high yield would be a welcome contribution to the art. This invention provides such a contribution.

SUMMARY OF THE INVENTION

This invention provides a catalytic enantioselective aldol synthesis of spiro-fused azetidinones.

Thus, this invention provides a process for producing a compound of the formula:

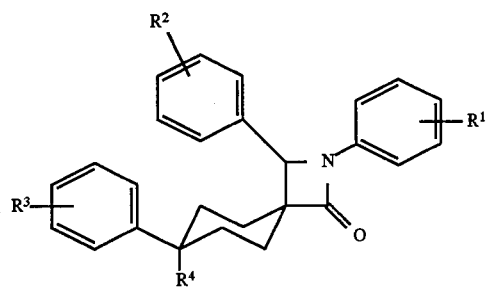
(1.0)

wherein:

$R^1$, $R^2$ and $R^3$ are each independently selected from:

(a) H;

(b) halo;

(c) —$OR^5$ wherein $R^5$ is selected from: H, $C_1$ to $C_6$ alkyl, aryl, aralkyl, alkaryl, heteroaryl, $C_2$ to $C_6$ alkenyl, $C_2$ to $C_6$ alkynyl, $C_3$ to $C_7$ cycloalkyl, $C_3$ to $C_7$ cycloalkenyl, or —C(O)$R^6$ (wherein $R^6$ is selected from $C_1$ to $C_6$ alkyl, aryl, or —$OR^7$ wherein $R^7$ is $C_1$ to $C_6$ alkyl or aryl); or (d) —C(O)$R^8$ wherein $R^8$ is selected from $C_1$ to $C_6$ alkyl, aryl, heteroaryl, aralkyl, cycloalkyl, —$OR^9$ (wherein $R^9$ is selected from $C_1$ to $C_6$ alkyl or aryl), or —N($R^{10}$)$_2$ (wherein each $R^{10}$ is independently selected from H, $C_1$ to $C_6$ alkyl or aryl);

$R^4$ is selected from H or —OH;

said process comprising:

(a) reacting, in a suitable organic solvent, a compound of formula:

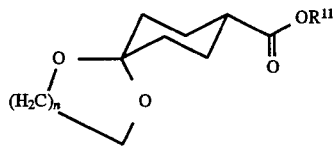
(2.0)

with an enolization base and a silylation reagent to produce a compound of the formula:

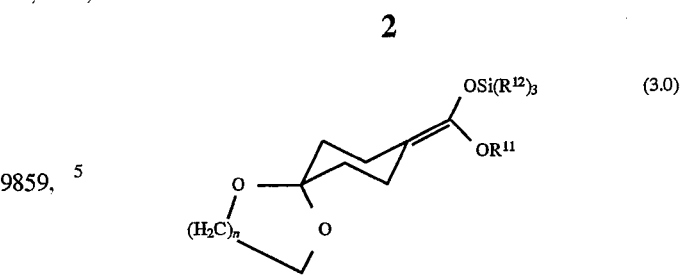
(3.0)

wherein n is 1 or 2, $R^{11}$ is a $C_1$ to $C_4$ alkyl group, and $R^{12}$ is a $C_1$ to $C_4$ alkyl group;

(b) reacting, in a suitable organic solvent, the compound of Formula 3.0 with a chiral catalyst and a compound of the formula:

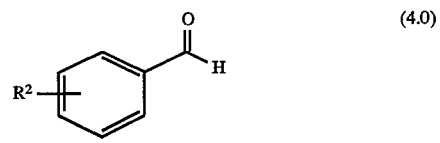
(4.0)

wherein $R^2$ is as defined above, with the proviso that $R^2$ is not OH, and then reacting the resulting product with a deprotecting reagent to remove the —Si($R^{12}$)$_3$ protecting group thereby forming a compound of the formula:

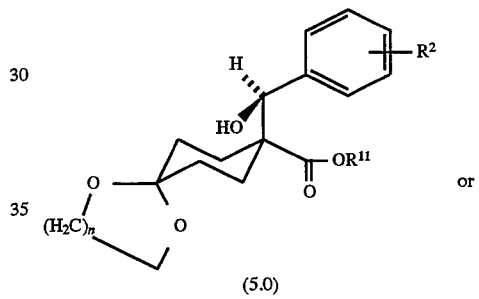
(5.0)

or

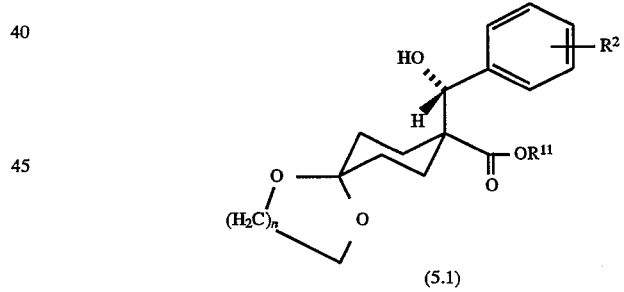
(5.1)

(or an enantiomeric mixture of 5.0 or 5.1); said chiral catalyst being a complex with borane and a compound of the formula:

(6.0)

wherein $R^{13}$ is selected from aryl or fused aryl, and $R^{14}$ represents an amino acid bound to the sulfur of Formula 6.0 through the nitrogen of the amino acid —C(H)(NH$_2$)COOH group;

(c) reacting a compound of Formula 5.0 or 5.1 (or an enantiomeric mixture of 5.0 and 5.1), in a suitable organic solvent, with a compound of the formula:

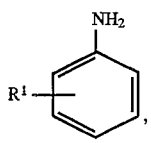
(7.0)

wherein $R^1$ is as defined above, with the proviso that $R^1$ is not OH, with a Lewis acid and with a strong acid, to produce a compound of the formula:

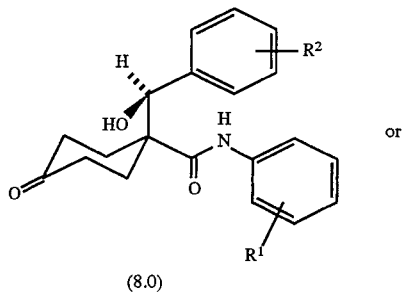

(or an enantiomeric mixture of 8.0 and 8.1);

(d) reacting a compound of Formula 8.0 or 8.1 (or enantiomeric mixtures thereof), in a suitable solvent, with a reagent that converts a —OH group into a leaving group, with a strong base, and with a phase transfer catalyst, to produce a compound of the formula:

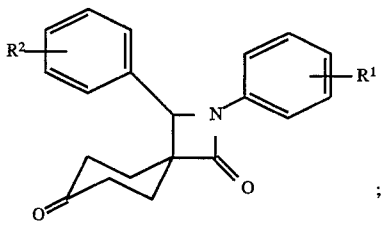

(e) reacting a compound of Formula 9.0, in a suitable solvent, with a compound of the formula:

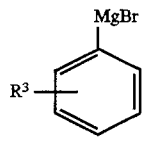
(10.0)

wherein $R^3$ is as defined above, with the proviso that $R^3$ is not OH, to produce a compound of the formula:

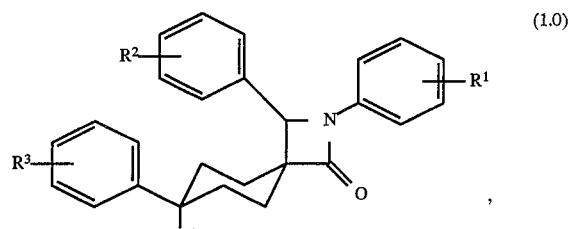
(1.0)

with the proviso that $R^1$, $R^2$ and $R^3$ am not —OH;

(f) when $R^1$, $R^2$, and/or $R^3$ (i.e., when one or more of $R^1$, $R^2$, and $R^3$) in Formula 1.0 in (e) above is —$OR^5$, wherein $R^5$ is an aralkyl group, optionally hydrogenating said compound of Formula 1.0 in a suitable alkanol solvent with a hydrogenation catalyst and a suitable Lewis acid, thereby convening said —$OR^5$ to —OH; and (g) when $R^4$ is —OH, optionally converting said —OH $R^4$ substituent to H by heating a compound of Formula 1.0 (wherein $R^4$ is —OH) with an acid to produce a dehydrated compound of Formula 1.2:

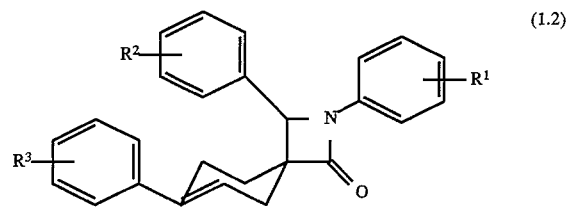

and then hydrogenating the compound of Formula 1.2 in a $C_1$ to $C_6$ alkanol solvent using a hydrogenation catalyst to produce a compound of Formula 1.0 wherein $R^4$ is H.

This invention also provides a process for producing a compound of the formula:

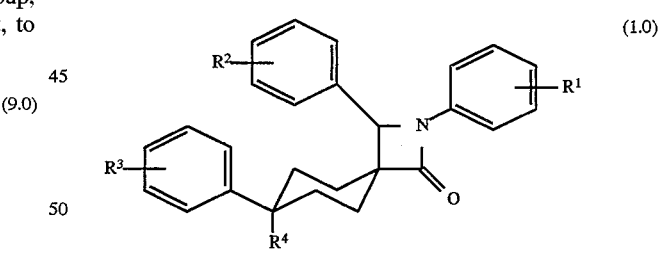

wherein $R^1$, $R^2$, $R^3$ and $R^4$ are as defined above, end with the proviso that at least one of $R^1$, $R^2$ and $R^3$ is OH, said process comprising: hydrogenating a compound of Formula 1.0 in a suitable alkanol solvent, wherein at least one of $R^1$, $R^2$ and $R^3$ is —$OR^5$, respectively, said $R^5$ substituent being an aralkyl protecting group, with a hydrogenation catalyst and a suitable Lewis acid (such as, for example. $MgX_2$, $TiX_4$, or $ZnX_2$, wherein X is Cl or Br, with $ZnX_2$ being preferred and $ZnBr_2$ being most preferred), thereby converting said —$OR^5$ to —OH. Step (g), described above, can then be carried out to convert an $R^4$ —OH group to an $R^4$ H.

This invention further provides a process for producing a compound of the formula:

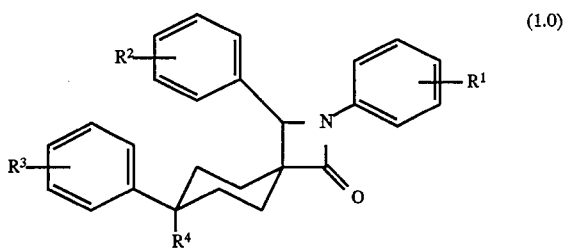

(1.0)

wherein $R^1$, $R^2$, $R^3$ and $R^4$ are as defined above, and with the proviso that at least one of $R^1$, $R^2$ and $R^3$ is OH and at least one of the remaining $R^1$, $R^2$ and $R^3$ is halo, said process comprising: hydrogenating a compound of Formula 1.0 in an a suitable alkanol solvent, wherein at least one of $R^1$, $R^2$ and $R^3$ is —$OR^5$, said $R^5$ substituent being an aralkyl protecting group, with a hydrogenation catalyst and a suitable Lewis acid (such as, for example, $MgX_2$, $TiX_4$, or $ZnX_2$, wherein X is Cl or Br, with $ZnX_2$ being preferred and $ZnBr_2$ being most preferred), thereby converting said —$OR^5$ to —OH. Step (g), described above, can then be carried out to convert an $R^4$—OH group to an $R^4$ H.

In addition this invention also provides a process for producing a compound of the formula:

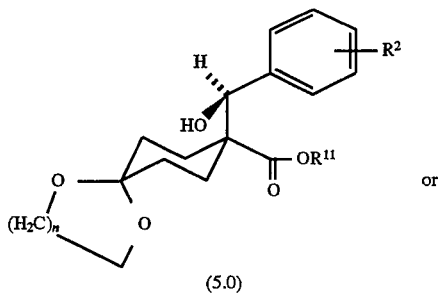

(5.0)

or

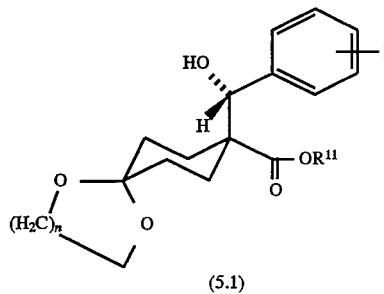

(5.1)

(or an enantiomeric mixture of 5.0 and 5.1) wherein n and $R^2$ are as defined above, with the proviso that $R^2$ is not OH, by reacting, in a suitable organic solvent, the compound of Formula 3.0 with a chiral catalyst and a compound of the formula:

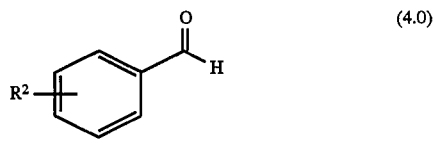

(4.0)

wherein $R^2$ is defined above, with the proviso that $R^2$ is not OH, and then reacting the resulting product with a deprotecting reagent to remove the —$Si(R^{12})_3$ protecting group; said chiral catalyst being a complex with boron and a compound of the formula:

(6.0)

wherein $R^{13}$ is selected from aryl or fused aryl, and $R^{14}$ represents an amino acid bound to the sulfur of Formula 6.0 through the nitrogen of the amino acid —$C(H)(NH_2)COOH$ group.

DETAILED DESCRIPTION OF THE INVENTION

The following terms, as used herein, have the following meanings, unless indicated otherwise:

alkyl—represents straight and branched carbon chains and contains from one to twenty carbon atoms, preferably one to six carbon atoms;

alkaryl—represents an aryl group, as defined below, in which an alkyl group, as defined above, is substituted for one of the aryl H atoms alkenyl—represents straight of branched carbon chains having at least one carbon to carbon double bond and preferably having from 2 to 6 carbon atoms;

alkynyl—represents straight or branched carbon chains having at least one carbon to carbon triple bond and preferably having from 2 to 6 carbon atoms;

aralkyl—represents an alkyl group, as defined above, in which an aryl group as defined below Is substituted for one of the alkyl H atoms, e.g., benzyl, 4-nitrobenzyl, 4-methoxybenzyl, and 4-chlorobenzyl;

aryl (including substituted aryl)—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, $CF_3$, amino, alkylamino, dialkylamino, or —$NO_2$;

cycloalkyl—represents a saturated carbocyclic ring having from 3 to 8 carbon atoms;

cycloalkenyl—represents a carbocyclic ring having from 3 to 8 carbon atoms and at least one carbon to carbon double bond in the ring;

—C(O)-represents the structure

fused aryl—represents one or more aryl rings, as defined above, fused together, e.g., a radical of naphthalene, such as an α-naphthyl or β-naphthyl (such as a 1-, 2-, 3-, 4-, 5-, 6-, 7-, or 8-naphthyl), or a radical of anthracene (such as 1-, 2-, 3-, 4- or 9-anthryl), or a radical of phenanthrene (such as 1-, 2-, 3-, 4: of 10-phenanthryl);

halo (halogen)—represents Cl, F, Br and I;

heteroaryl—represents cyclic groups having at least one (i.e., one or more) heteroatoms, selected from O, S or N, interrupting a carbocyclic ring structure and having a sufficient number of delocalized pi electrons to provide aromatic character, with the aromatic heterocyclic groups preferably containing from 2 to 14 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1, 2,4-thiadizolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, etc. Preferred heteroaryl groups are pyridyl, 2- or 3-furyl, or 3-thienyl, 2-, 4- or 5-imidazolyl or 7-indolyl; and substituted aryl, substituted benzyl, substituted phenyl, or substituted heteroaryl - an aryl, benzyl, phenyl or heteroaryl, repectively, wherein one or more aromatic hydrogens are replaced by the same or different substituents independently selected from hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_p R^a$ (wherein p is 0, 1 or 2 and $R^a$ is alkyl having from 1 to 6 carbon atoms).

Each reaction of the processes of the invention takes place at suitable temperature or within a suitable temperature range. A suitable temperature is a temperature (or temperature range) that allows the reaction to proceed at a reasonable rate without the formation of an excessive amount of by-products and without the production of an excessive amount of degradation products.

A suitable solvent is a solvent in which the reactants are suitably soluble in or in which the reactants are in sufficient contact with each other, to allow the reaction to proceed at a reasonable rate. The solvents used herein are used in amounts suitable to provide a reaction medium which allows the reaction to proceed at a reasonable rate.

Those reactions which are not disclosed as being carried out under an inert atmosphere (e.g., nitrogen), can, if desired, be carried out under an inert atmosphere. Those skilled in the art will appreciate that it is desirable to carry out a reaction under an inert atmosphere when reagents are used which are known to be unstable when exposed to air (e.g., $(CH_3)_3Al$ and the Grignard reagent).

Preferably, the compounds produced by the processes of this invention contain the $R^1$, $R^2$, and $R^3$ substituents in the para position of their respective phenyl rings. Thus, this invention preferably provides a process for producing a compound of the formula:

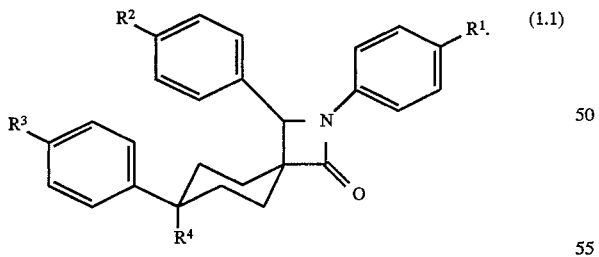

(1.1)

To produce the compounds of Formula 1.1 by the processes of the invention, compounds of the formulas:

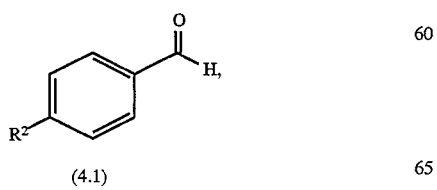

(4.1)

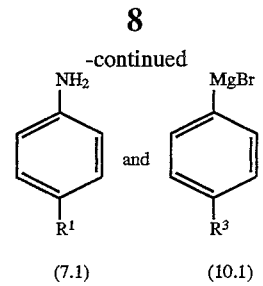

(7.1)    (10.1)

are used instead of compounds of Formulas 4.0, 7.0 and 10.0, respectively. In so doing, intermediate compounds of formulas:

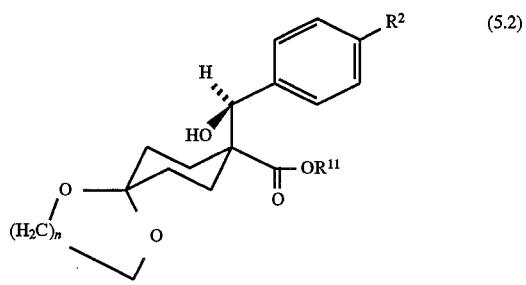

(5.2)

or

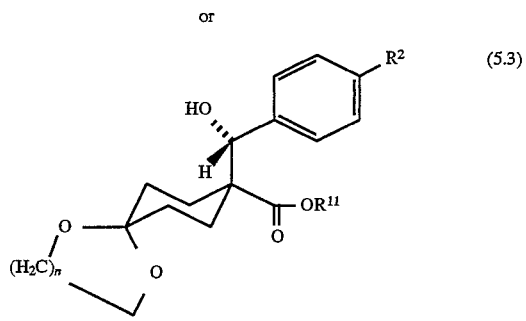

(5.3)

(or an enantiomeric mixture of 5.2 and 5.3) are produced instead of Formulas 5.0 or 5.1, respectively. Preferably, n is 1; therefore, intermediate compounds of formulas:

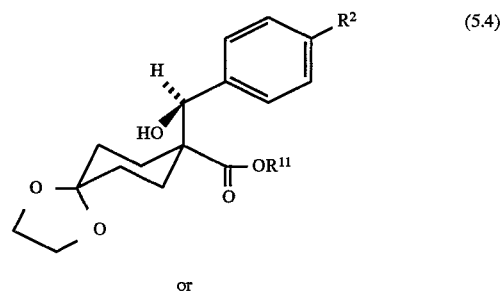

(5.4)

or

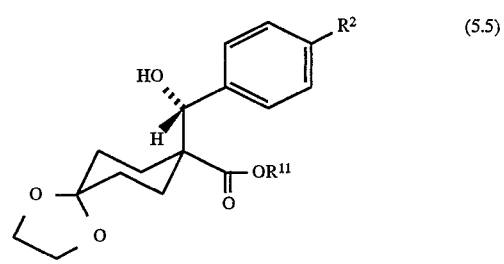

(5.5)

(or an enantiomeric mixture of 5.4 and 5.5) are preferably produced. Intermediate compounds of the formulas:

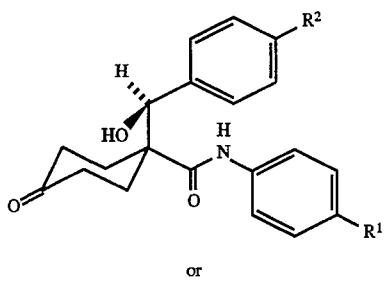 (8.2)

or

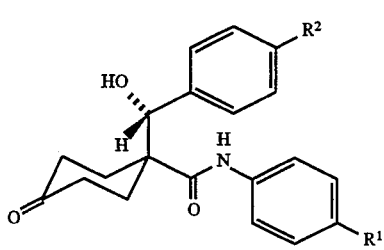 (8.3)

(or an enantiomeric mixture of 8.2 and 8.3) am produced instead of Formulas 8.0 and 8.1, respectively. Also, intermediate compounds of the formula:

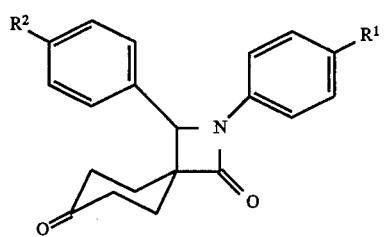 (9.1)

are produced instead of Formula 9.0.

Those skilled in the art will appreciate that when n is 1, the intermediate

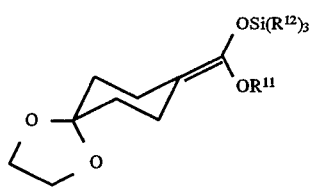 (3.1)

is produced from starting reactant

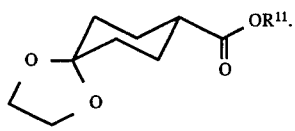 (2.1)

Preferably, for the compounds of Formulas 1.0 and 1.1, $R^1$ is, as stated above, in the para position of the phenyl ring, and is selected from H, halo, or —$OR^5$ wherein $R^5$ is selected from H, $C_1$ to $C_6$ alkyl or aralkyl. Most preferably, $R^1$ is selected from H, Cl, F or —$OR^5$ wherein $R^5$ is $C_1$ to $C_6$ alkyl; more preferably, H, Cl, F or —$OCH_3$; still more preferably, H or F; and even more preferably, F.

Preferably, for the compounds of Formulas 1.0 and 1.1, $R^2$ is, as stated above, in the para position of the phenyl ring, and is selected from H, halo, or —$OR^5$ wherein $R^5$ is selected from H, $C_1$ to $C_6$ alkyl or aralkyl. Most preferably, $R^2$ is selected from H, —OH or —$OR^5$ wherein $R^5$ is $C_1$ to $C_6$ alkyl or aralkyl; more preferably, H, —OH, benzyloxy (i.e., —$OCH_2C_6H_5$), 4-chlorobenzyloxy, 4-nitrobenzyloxy, 4-methoxybenzyloxy or —$OCH_3$; still more preferably, —OH or —$OCH_3$; and even more preferably, —OH.

Preferably, for the compounds of Formulas 1.0 and 1.1, $R^3$ is, as stated above, in the pare position of the phenyl ring, and is selected from H, halo, or —$OR^5$ wherein $R^5$ is selected from H, $C_1$ to $C_6$ alkyl or aralkyl. Most preferably, $R_3$ is selected from H, Cl, F or —$OR^5$ wherein $R^5$ is $C_1$ to $C_6$ alkyl; more preferably, H, Cl, F or —$OCH_3$; and still more preferably, Cl.

Preferably, $R^4$ is —OH

Examples of compounds produced by the processes of this invention include:

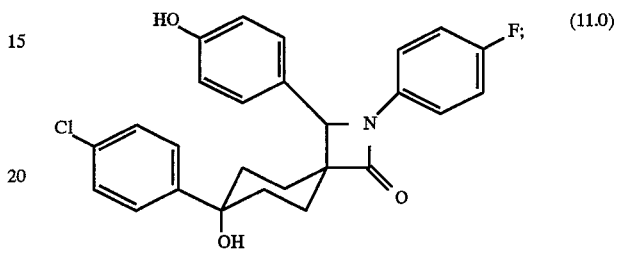 (11.0)

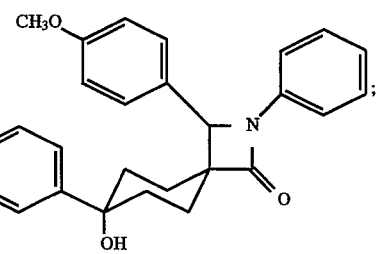 (12.0)

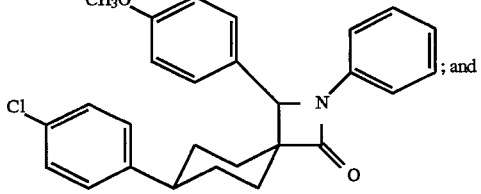 (13.0)

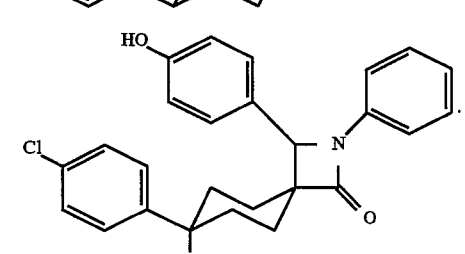 (14.0)

Additional examples are disclosed in WO 94/17038, published Aug. 4, 1994, the disclosure of which is Incorporated herein by reference thereto.

The starting reactant, Formula 2.0, can be produced by methods well known in the art. For example, catalytic hydrogenation of a ($C_1$ to $C_4$ alkyl) 4-hydroxy benzoate (Formula 15.0) with 5% Rh on alumina gives the ($C_1$ to $C_4$ alkyl) 4-hydroxy cyclohexanoate (Formula 16.0). Oxidation of Formula 16.0 with bleach yields the ketone ester (17.0). The protection of the ketone group is achieved with ethylene glycol (when n is 1 in Formula 2.0) or propylene glycol (when n is 2 in Formula 2.0) in the presence of an acid catalyst (e.g., p-$CH_3C_6H_4SO_2H$ or HCl). The reaction sequence can be represented as:

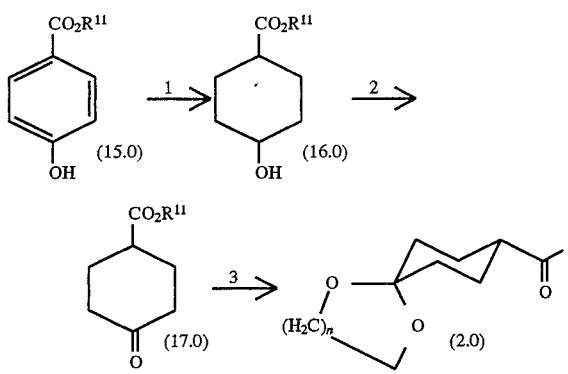

Step 1 represents reaction with H₂/5% Rh on alumina; Step 2 represents reaction with bleach (i.e., aqueous sodium hypochlorite) and acetic acid; and Step 3 represents reaction with ethylene glycol (or propylene glycol) with p-toluenesulfonic acid in a suitable organic solvent such as toluene. Preferably, n is I (i.e., ethylene glycol is used) so that a compound of Formula 2.1 is produced. Most preferably, n is I and $R^{11}$ is ethyl so that a compound of formula:

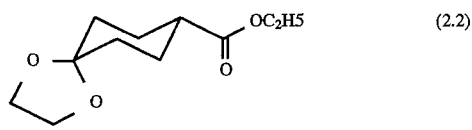

is obtained.

In reaction Step (a), a compound of Formula 2.0 is reacted, under an inert atmosphere such as nitrogen, with an enolization base and a silylation reagent to produce a compound of Formula 3.0. Preferably, as stated above, n is 1 so a Formula of 3.1 is produced. Most preferably, n is 1, $R^{11}$ is ethyl, and $R^{12}$ is methyl so that a compound of formula:

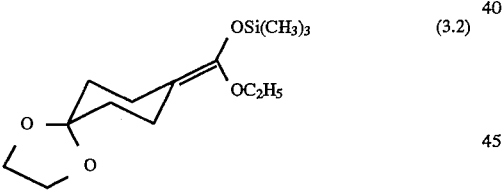

is obtained. Examples of suitable organic solvents include but are not limited to: hexane, THF (tetrahydrofuran), pentane, toluene and mixtures thereof. When mixtures of solvents are used, THF is mixed with pentane or hexane, or toluene is mixed with pentane or hexane. The ratio of solvents, (THF or toluene):(pentane or hexane) is about 1:0.4 to about 1:0.9, with about 1:0.6 to about 1:0.9 being preferred, and about 1:0.8 being most preferred. Preferably, THF/hexane (i.e., a mixture) is used as the solvent. The reaction is conducted at a temperature of about −78° to about 0° C. with about −50° to about −10° C. being preferred, and about −30° to about −15° C. being most preferred.

The enolization base in Step (a) is used in an amount of about 1.0 to about 1.5 equivalents, with about 1.0 to about 1.4 equivalents being preferred, and about 1.1 to about 1.3 equivalents being most preferred. Examples of suitable enolization bases include but are not limited to: $LiN(R^{15})_2$, KO-t-$C_4H_9$, $NaH_2$, sec-butyl lithium, t-butyl lithium, and lithium bis(trimethylsilyl)amide (i.e., $((CH_3)_3Si)_2NLi)$. Each $R^{15}$ is independently selected from a $C_1$ to $C_6$ alkyl, and preferably each $R^{15}$ is i-$C_3H_7$. Preferably, the enolization base is selected from $LiN(i-C_3H_7)_2$ or KO-t-$C_4H_9$, with $LiN(i-C_3H_7)2$ being most preferred.

The silylation reagent in Step (a) is used in an amount of about 1.0 to about 2.0 equivalents, with about 1.2 to about 1.8 equivalents being preferred, and about 1.4 to about 1.6 equivalents being most preferred. Suitable silylation reagents are represented by the formula $(R12)3SiR^{16}$ wherein $R^{12}$ is a $C_1$ to $C_4$ alkyl group (e.g., methyl, ethyl or t-butyl), and $R^{16}$ is Cl, Br, or I. Preferably, $R^{12}$ is methyl and $R^{16}$ is Cl. Examples of silylation reagents include but are not limited to: $(CH_3)_3SiCl$, $(C_2H_5)_3SiCl$, $(t-C_4H_9)(CH_3)_2SiCl$, and $CH_3C(=NSi(CH_3)_3)OSi(CH_3)_3$. Preferably, $(CH_3)_3SiCl$ is used.

Preferably, the reaction product from Step (a) is isolated before proceeding to Step (b). For example, the reaction mixture is vacuum distilled to obtain the reaction product of Step (a).

In Step (b) a compound of Formula 3.0 (or 3.1 or 3.2) is reacted, 5 under an inert atmosphere such as nitrogen, with a compound of Formula 4.0 (or 4.1) in the presence of a chiral catalyst to produce the intermediates:

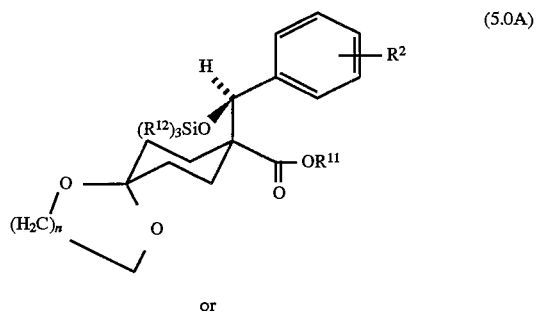

or

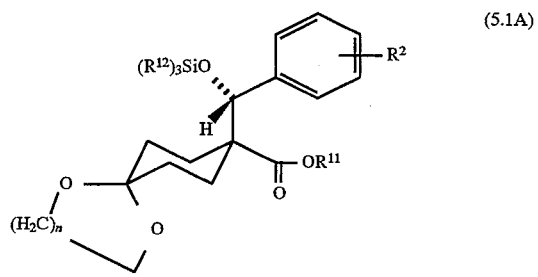

(or an enantiomeric mixture of 5.0A and 5.1A). When the preferred substituents are used, intermediates of the formulas:

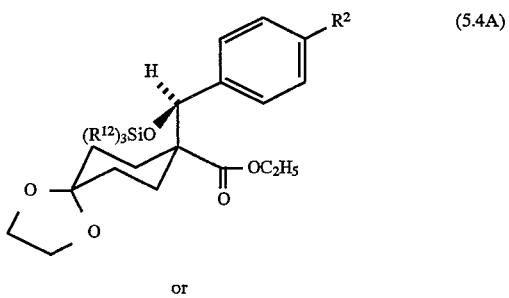

or

-continued

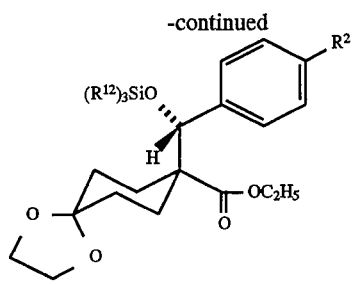
(5.5A)

(or an enantiomeric mixture of 5.4A and 5.5A) am obtained. Further reaction with a deprotecting reagent removes the silyl protecting group (—Si($R^{12}$)$_3$) to produce a compound of Formula 5.0, 5.1, 5.2, 5.3, 5.4, or 5.5 (or the enantiomeric mixture of 5.0 and 5.1, 5.2 and 5.3, or 5.4 and 5.5).

Suitable organic solvents for the reaction in Step (b) include but are not limited to: propionitrile, nitromethane, acetonitrile, benzonitrile, nitrobenzene and $CH_2Cl_2$. Preferably, propionitrile, nitromethane or acetonitrile is used, and most preferably propionitrile is used. The reaction of a compound of Formula 3.0 with a compound of Formula 4.0 followed by deprotection of the resulting product in Step (b) is conducted at a temperature of about −80° to about −30° C. with about −80° to about −50° C. being preferred, and about −78° to about −65° C. being most preferred.

In Step (b), a compound of Formula 4.0 is used in an amount of about 0.8 to about 1.2 equivalents, with about 0.9 to about 1.1 equivalents being preferred, and about 1.0 to about 1.05 equivalents being most preferred.

The chiral catalyst is a complex formed from borane and a compound of Formula 6.0. The complex used can be an individual enantiomer or the mixture of enantiomers formed when the borane reagent is reacted with the compound of Formula 6.0 to produce the complex. The complex can be formed before addition to the reaction mixture or can be formed in situ in the reaction mixture. Preferably, the complex is formed in situ. The complex is formed by mixing (reacting) a borane reagent (e.g., $BH_3$.THF, $BH_3$.($CH_3$)$_2$S or $B_2H_6$) with a compound of Formula 6.0. When the complex is formed in situ, the compound of Formula 6.0 is added to the reaction mixture and then the borane reagent is added to the reaction mixture. Preferably, $BH_3$.THF or $BH_3$.($CH_3$)$_2$S is used, with $BH_3$.THF being most preferred. The boron reagent is used in an amount of about 0.8 to about 1.2 equivalents, preferably about 0.9 to about 1.1 equivalents and most preferably about 0.9 to about 1.0 equivalents.

Preferably, $R^{13}$ is a substituted phenyl group or a naphthyl group. The naphthyl group is bound to the sulfur atom through a β carbon, i.e., $R^{13}$ is a 2-, 3-, 6- or 7-naphthyl group. Examples of $R^{13}$ include but are not limited to: 4-nitrophenyl, 2,4,6-trimethlyphenyl and 2-naphthyl.

$R^{14}$ represents a radical of an amino acid (i.e., an α-amino carboxylic acid) wherein the radical is bound to the sulfur through the α-amino group of the amino acid, i.e., $R^{14}$ represents

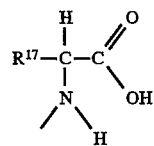

wherein $R^{17}$ represents the remaining portion of the amino acid. The amino acids useable in the processes of the invention do not include those containing a second carboxylic group or a second basic group (e.g., amino). Thus, the acidic amino acids and the basic amino acids are excluded. Suitable amino acids include but are not limited to: valine, 3,3-dimethyl-2-amino-butanoic acid, tryptophan, phenylglycine and phenyl-alanine. Preferably, valine, phenylglycine or tryptophan are used.

Examples of compounds of Formula 6.0 include but are not limited to:

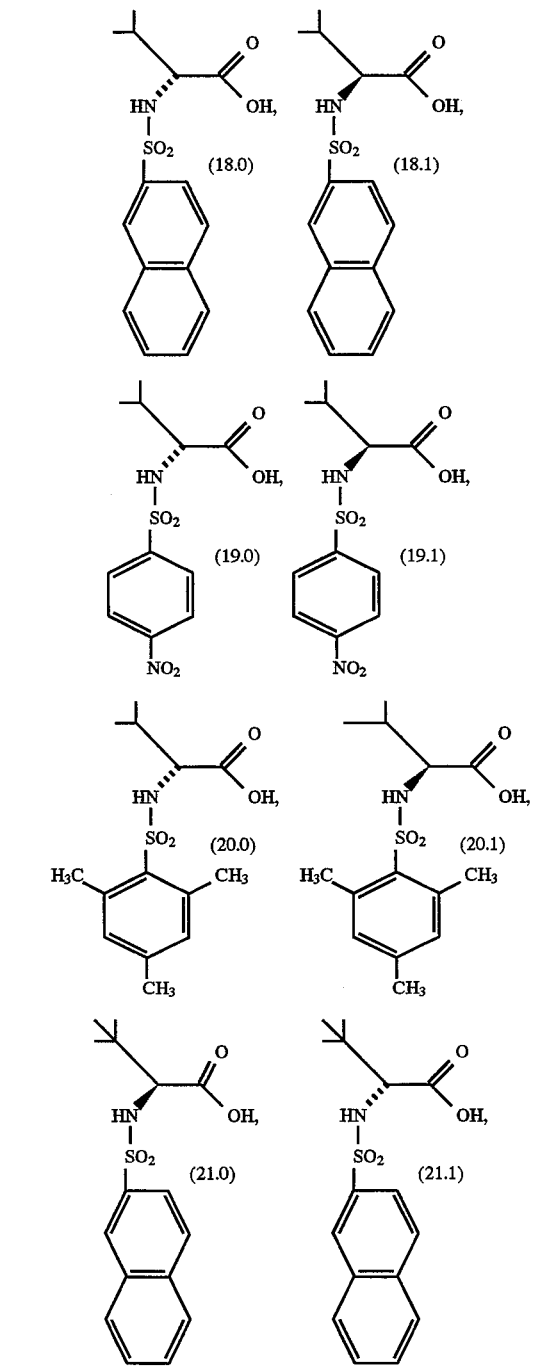

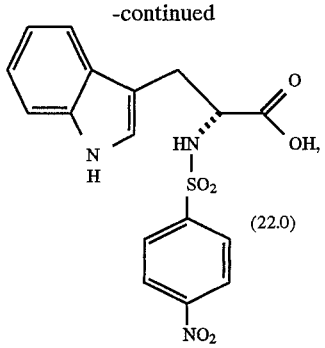

(22.0)

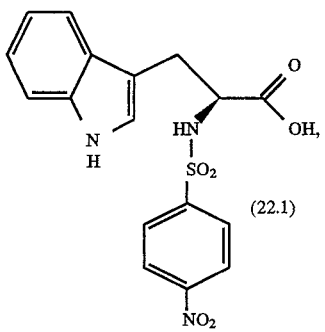

(22.1)

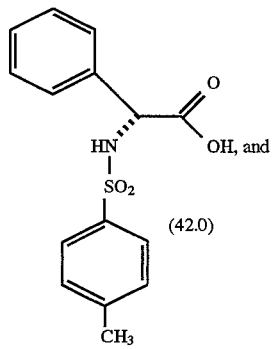

(42.0)

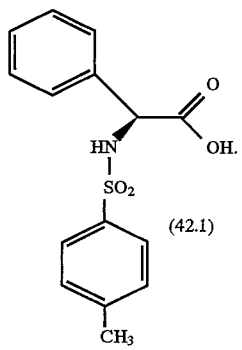

(42.1)

Preferably, 18.0, 19.0, 20.0, 21.0 or 22.0 is used. Most preferably, 18.0 is used.

The compounds of Formula 6.0 can be obtained in high yield and high purity by reacting at a suitable temperature, in a suitable solvent, the amino acid with $R^{13}SO_2Cl$ with a mild base. The reaction mixture is then acidified with an acid such as aqueous HCl, $H_2SO_4$, acetic acid or $H_3PO_4$, with aqueous HCl being preferred. After acidification, the compound of Formula 6.0 can be filtered and recovered, or the compound of Formula 6.0 can be extracted into a suitable ether solvent such as t-butyl methyl ether or diethyl ether. The compound of Formula 6.0 is then obtained by concentration of the ether solutions, crystallization (by techniques well known in the art) and filtration.

The reaction producing the compound of Formula 6.0 is conducted at a temperature of about $-20°$ to about $40°$ C., with about $-10°$ to about $30°$ C. being preferred, and about $5°$ to about $25°$ C. being most preferred. Suitable bases include, for example, $(CH_3)_3N$, $(C_2H_5)_3N$ and $NaHCO_3$, with $(C_2H_5)_3N$ being preferred. Suitable solvents include, for example, mixtures of $THF/H_2O$, $CH_3CN/H_2O$ and acetone/$H_2O$, with $THF/H_2O$ being preferred. The ratio of organic solvent (e.g., $CH_3CN$ or THF) to water is about 1:1.5 to about 1:3.5, with about 1:2.0 to about 1:3.0 being preferred, and about 1:2.5 being most preferred.

In the reaction producing compound 6.0, about 0.9 to about 1.2 equivalents of amino acid is used, with about 0.95 to about 1.1 equivalents being preferred, and about 1.0 to about 1.05 equivalents being most preferred. The reactant $R^{13}SO_2Cl$ is used in amounts of about 0.9 to about 1.2 equivalents, with about 0.95 to about 1.1 equivalents being preferred, and about 1.0 to about 1.05 equivalents being most preferred.

The compound of Formula 6.0, to form the complex with the borane reagent, is used in an amount of about 0.8 to about 1.1 equivalents, preferably about 0.9 to about 1.05 equivalents, and most preferably about 0.9 to about 0.95 equivalents.

The complex is formed between the nitrogen of the amino group and the —OH of the carboxylic group of Formula 6.0 thus producing a five membered ring:

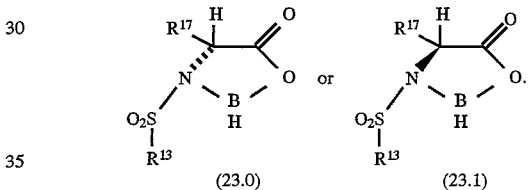

(23.0)      (23.1)

Examples of the boron complexes used as chiral catalysts include:

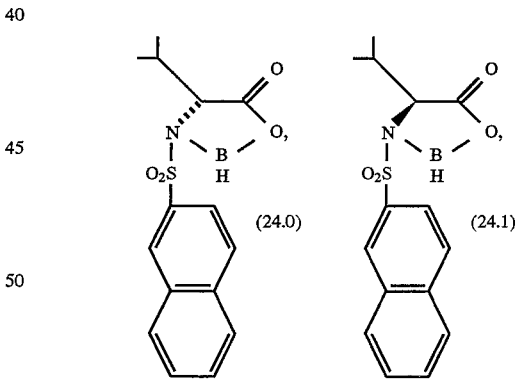

(24.0)      (24.1)

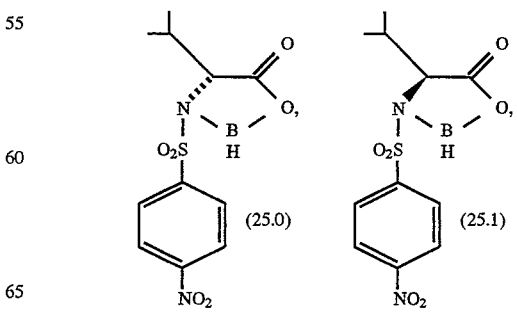

(25.0)      (25.1)

-continued

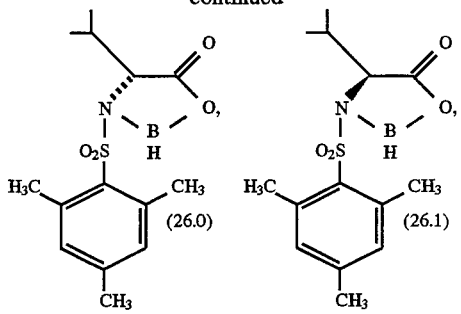

(26.0) (26.1)

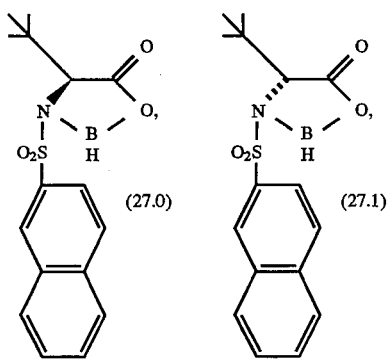

(27.0) (27.1)

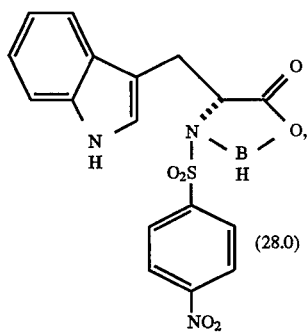

(28.0)

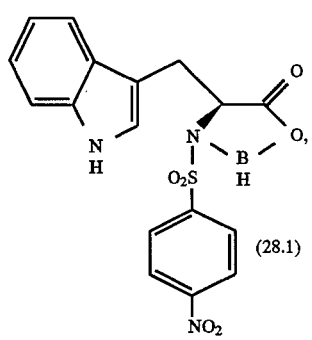

(28.1)

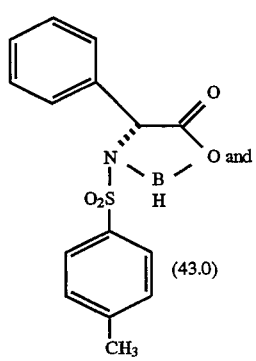

(43.0)

-continued

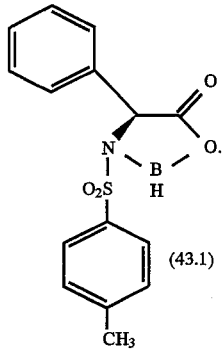

(43.1)

After the aldol condensation is complete, the protected intermediate 5.0A or 5.1A (e.g., 5.4A or 5.5A) is produced. Before deprotection of the intermediate, the reaction mixture is quenched with an aqueous NaHCO3 solution (preferably a saturated solution). Quenching the reaction mixture converts the chiral catalyst (borane complex) to the sodium salt of a compound of Formula 6.0, i.e.,

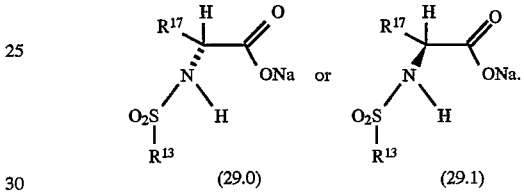

(29.0) (29.1)

The aqueous layer containing the sodium salt is separated from the organic layer containing a compound of Formula 5.0 or 5.1. Acidification of the aqueous layer with acid produces the compound of 6.0, or extraction with an ether (e.g., $(C_2H_5)_2O$, $(CH_3)_2O$ or $(t-C_4H_9)O(CH_3)$, and preferably $(t-C_4H_9)O(CH_3)$) produces the compound of 6.0, i.e., a compound of the formula:

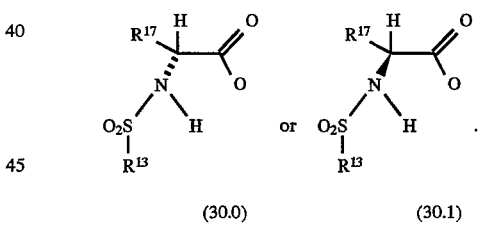

(30.0) (30.1)

After catalyst recovery, the protecting silyl group, —S($R^{12}$)$_3$, is removed (i.e, the intermediate is deprotected) by the addition of a deprotecting reagent selected from: tetrabutylammonium fluoride, NaF or benzyltrimethylammonium fluoride. Preferably, tetrabutylammonium fluoride is used. The deprotecting reagent is mixed with a suitable organic solvent before addition to the reaction mixture. Suitable organic solvents include, for example, THF, toluene or methylene chloride. Preferably, THF is used. The deprotection reaction is conducted at a temperature of about 0° to about 30° C., with about 10° to about 25° C. being preferred, and about 20° to about 25° C. being most preferred. The deprotecting reagent is used in an amount of about 0.5 to about 1.0 equivalents, with about 0.6 to about 0.9 equivalents being preferred, and about 0.7 to about 0.8 equivalents being most preferred.

Preferably, the reaction product of Step (b) is isolated before proceeding to Step (c). For example, the reaction product of Step (b) can be crystallized out of solution using a suitable organic solvent such as toluene or ethyl acetate.

Suitable organic solvents for Step (c) include, for example, methylene chloride, hexane, toluene and mixtures thereof. Preferably, methylene chloride is used.

The reaction in Step (c) is conducted at a temperature of about 20° to about 100° C., with about 40° to about 80° C. being preferrred, and about 50° to about 60° C. being most preferred.

The compound of Formula 7.0 (or 7.1) is used in an amount of about 1.5 to about 6.0 equivalents, with about 2.0 to about 5.0 equivalents being preferred, and about 3.0 to about 4.0 equivalents being most preferred.

Examples of Lewis acids useable in Step (c) include but are not limited to: $(CH_3)_3Al$, $(C_2H_5)_3Al$ and $Cl_3Al$, with $(CH3)3Al$ being preferred. The Lewis acid is used in an amount of about 1.0 to about 6.0 equivalents, with about 2.0 to about 5.0 equivalents being preferred, and about 3.0 to about 4.0 equivalents being most preferred.

Examples of strong acids suitable for use in Step (c) include, for example, HCl, $H_2SO_4$, $CF_3CO_2H$ and $CH_3SO_3H$. Preferably, aqueous HCl, $H_2SO_4$, or $CF_3CO_2H$ is used, with aqueous HCl being most preferred. In Step (d), the product of Step (c) is reacted, in a suitable solvent, with a reagent that converts a hydroxy group into a leaving group, a strong base and a phase transfer reagent to produce the intermediate compound of Formula 9.0. The solvent used is a mixture of water with a solvent selected from, for example, methylene chloride, toluene or t-butyl methyl ether. The ratio of water to solvent is about 1:1 to about 1:8, with about 1:2 to about 1:6 being preferred, and about 1:3 to about 1:5 being most preferred, and about 1:4 being even more preferred. Preferably, methylene chloride mixed with water is used as the solvent.

The reaction in Step (d) is conducted at a temperature of about 0° to about 60° C., with about 20° to about 50° C. being preferred, and about 30° to about 40° C. being most preferred.

Examples of the reagents that convert a hydroxy group into a leaving group in Step (d) include, for example, the Mitsunobu reagents (a triarylphosphine or a trialkylphosphine mixed with diethylazodi-carboxylate, such as triphenylphosphine mixed diethylazodicarboxylate), $(C_2H_5O)_2P(O)Cl$, 2,4,6-trichlorobenzoyl chloride, 2,6-dichlorobenzoyl chloride, $CH_3SO_2Cl$ and p-toluenesulfonyl chloride (TsCl). Preferably, $(C_2H_5O)_2P(O)Cl$, 2,4,6-trichlorobenzoyl chloride, or 2,6-dichlorobenzoyl chloride are used, with $(C_2H_5O)_2P(O)Cl$ being most preferred. The reagent that converts a hydroxy group into a leaving group is used in an amount of about 1.0 to about 2.0 equivalents, with about 1.2 to about 1.8 equivalents being preferred, and about 1.3 to about 1.6 equivalents being most preferred.

Strong bases utilizable in Step (d) include, for example, NaOH, $NaOCH_2$, KOH, $KOCH_3$, $KO-t-C_4H_9$ and $NaO-t-C_4H_9$. Preferably, NaOH, $NaOCH_2$, KOH, $KOCH_3$, or $KO-t-C_4H_9$ is used, with NaOH being preferred. The base is used in an amount of about 10 to about 50 equivalents, with about 20 to about 40 equivalents being preferred, and about 25 to about 30 equivalents being most preferred.

In Step (d), a phase transfer catalyst is used in an amount of about 0.01 to about 1.0 equivalents, with about 0.05 to about 0.6 equivalents being preferred, and about 0.1 to about 0.3 equivalents being most preferred. Examples of useable phase transfer catalysts include but are not limited to: $C_6H_5CH_2N(C_2H_5)_3Cl$, $C_6H_5CH_2N(C_2H_5)_3Br$, tetrabutyl-ammonium sulfate, tetrabutylammonium acetate, tetrabutylammonium chloride, tetrabutylammonium iodide, benzyl-tributylphosphorous chloride, tetrabutylammonium hydroxide, and tetraphenylphosphorous iodide. Preferably, $C_6H_5CH_2N(C_2H_5)_3Cl$ (benzyltriethylammonium chloride), $C_6H_5CH_2N(C_2H_5)_3Br$ (benzyltriethylammonium bromide), tetrabutyl-ammonium sulfate, tetrabutylammonium acetate or tetrabutylammonium chloride is used, with $C_6H_5CH_2N(C_2H_5)_3Cl$ being most preferred.

The reaction mixture in Step (d) is quenched into an ice-cold HCl solution, and extracted With a suitable organic solvent, such as ethyl acetate, $CH_2Cl_2$, toluene, or $(C_2H_5)_2O$, with ethyl acetate or toluene being preferred, and ethyl acetate being most preferred. Concentration of the organic solvent solution followed by addition of $(C_2H_5)_2O$ or t-butyl methyl ether, preferably $(C_2H_5)_2O$, produces the compound of Formula 9.0. Generally, the compound of Formula 9.0 is obtained as crystals.

In Step (e), the intermediate from Step (d) is reacted with a compound of 10.0 or 10.1. This reaction is a diastereoselective reverse Grignard addition. In this reaction the ketone intermediate (9.0 or 9.1) from Step (d) is added slowly (e.g., dropwise) to the Grignard reagent of Formula 10.0 or 10.1. The dropwise addition usually is done at a rate of about 10 to about 60 ml/minute, preferably about 20 to about 50 ml/minute and most preferably about 30 to about 40 ml/minute. The Grignard reagent (10.0 or 10.1) is used in an amount of about 1.0 to about 2.0 equivalents, with about 1.2 to about 1.8 equivalents being preferred, and about 1.4 to about 1.6 equivalents being most preferred. The product from Step (d) (9.0 or 9.1) is used in an amount of about 1.0 equivalent. The reaction is conducted at a temperature of about 10° to about 80° C., with about 20° to about 70° C. being preferred, and about 40° to about 60° C. being most preferred.

The reaction mixture in Step (e) is quenched into ice-cold HCl solution and extracted with a suitable organic solvent. Examples of suitable organic solvents include, for example, ethyl acetate, toluene, and $(C_2H_5)_2O$, with ethyl acetate being most preferred. Concentration of the solvent yields the product of Step (e), i.e., a compound of Formula 1.0 (or 1.1). If desired, such as if Step (f) will not be carried out, the product of Step (e) can be isolated by techniques well known in the art. For example, the product of Step (e) can be isolated using silica gel column chromatography with a solvent to elute the desired product.

$R^1$, $R^2$ and $R^3$ in the compounds of Formulas 1.0 and 1.1 produced in Step (e) are not —OH. For one or more (i.e., at least one) of $R^1$, $R^2$ and $R^3$ to be —OH in the final product, the corresponding $R^1$, $R^2$ and/or $R^3$ group in the reactants of Formulas 7.0, 4.0 and/or 10.0 is a protected —OH group, i.e., an —$OR^5$ group wherein $R^5$ is aralkyl. Compounds of Formula 1.0 or 1.1 with these protected hydroxy groups are reacted according to the process of Step (f) to produce the corresponding compound of Formula 1.0 or 1.1 with the desired —OH group or groups. In the process of Step (f), when one or more of the remaining $R^1$, $R^2$ and $R^3$ groups are halo (e.g., Cl or F), dehalogenation does not take place when the protected hydroxy group is subjected to hydrogenation. Those skilled in the art will appreciate that because there is hydrogenation in this step, any substituents containing unsaturation will also be hydrogenated. Thus, it is desirable to avoid having one or more of the remaining $R^1$, $R^2$ and $R^3$ groups be an —$OR^5$ group wherein $R^5$ is alkenyl, alkynyl or cycloalkenyl.

Suitable aralkyl groups for $R^5$ in Step (f) include benzyl, 4-methoxybenzyl, 4-Cl-benzyl, and 4-$NO_2$-benzyl, with benzyl being preferred.

In the process of Step (f), a compound of Formula 1.0 or 1.1, having one or more of the protected hydroxy groups described above, is hydrogenated in a suitable alkanol solvent using a suitable hydrogenation catalyst, hydrogen, and a suitable Lewis acid to produce a compound of Formula 1.0 or 1.1 having one or more corresponding hydroxy groups. The hydrogenation reaction is generally conducted at room temperature (i.e., about 20° to about 25° C.). The compound of Formula 1.0 or 1.1 (having one or more protected hydroxy groups) is used in an amount of about 1.0 equivalent. Suitable alkanol solvents include the $C_1$ to $C_6$ alkanols, such as, for example, ethanol, methanol, n-propanol, iso-propanol, and n-butanol. Preferably, ethanol is used.

Suitable hydrogenation catalysts include, for example, Pd/C, Pt/C, Ni/C, Raney Nickel and PtO. Preferably, Pd/C, Pt/C or Ni/C is used, and most preferably Pd/C is used. The catalyst is used in an amount of about 5 to about 40 w/w %, with about 10 to about 20 w/w % being preferred. Hydrogenation is carried out at a pressure of about 5 to about 70 psi, with about 20 to about 60 psi being preferred, and about 40 to about 60 psi being most preferred.

In process Step (f), a Lewis acid is used. Without wishing to be bound by theory, it is believed that the presence of the Lewis acid prevents the dehalogenation of any of the remaining $R^1$, $R^2$ and $R^3$ groups which are halo. Examples of suitable Lewis acids include but are not limited to $ZnX_2$, $MgX_2$ or $TiX_4$, wherein X is Cl or Br. Preferably, a Lewis acid of the formula ZnX2 wherein X is Cl or Br, preferably Br, is used. The Lewis acid is used in an amount of about 0.2 to about 1.0 equivalents, with about 0.4 to about 0.9 equivalents being preferred, and about 0.7 to about 0.8 equivalents being most preferred. Other Lewis Acids which may prove useful include $AlCl_3$, $MgBr_2$ and $MnBr_2$.

In the above process compounds of Formula 1.0 are usually produced wherein $R^4$ is is —OH. Compounds wherein $R^4$ is —OH can be dehydrated using techniques well known in the art to produce compounds of Formula 1.0 wherein $R^4$ is H. Thus, the $R^4$ —OH group can be converted to H by heating a compound of Formula 1.0 (wherein $R^4$ is —OH) with an acid to produce a compound of Formula 1.2:

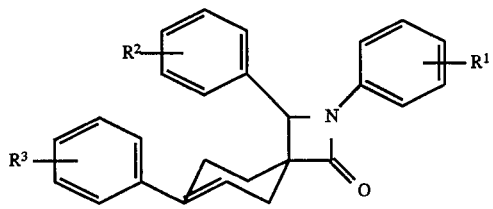

and preferably a compound of Formula 1.3:

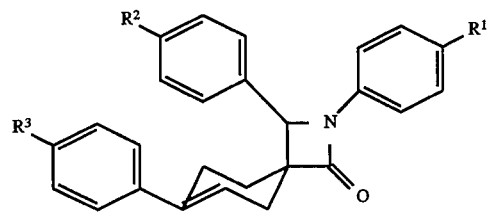

Suitable temperatures for the dehydration step are within the range of about 40° to about 100° C., with about 60° to about 90° C. being preferred, and about 70° to about 90° C. being most preferred. Examples of acids useable in the dehydration Step include, for example, sulfuric acid, HCl, p-toluenesulfonic acid and trifluoroacetic acid.

The compound of Formula 1.2 or 1.3 is then hydrogenated at room temperature (i.e., about 20° to about 25° C.), in a suitable alkanol solvent with a suitable hydrogenation catalyst to produce a compound of Formula 1.0 or 1.1, respectively, wherein $R^4$ is H. The alkanol solvent, hydrogenation catalyst, amounts and pressure used are as described above for the hydrogenation in Step (f).

The product of Step (f) can be isolated by techniques known in the art. For example, the product of Step (f) can be crystallized from solution using an organic solvent such as, for example, methylene chloride, ethanol/hexane (i.e., a mixture), or ethyl acetate/hexane (i.e., a mixture). If the conversion of $R^4$ from —OH to H is to be made, the product of Step (f) does not have to be isolated before performing the conversion step (Step (g)). If conversion to the $R^4$ H compound is carried out, the product so formed can be isolated as described for the isolation of the product of Step (f).

Those skilled in the art will appreciate that, unless stated otherwise, the compounds produced in the various process steps can, if desired, be separated from their reaction mixtures, isolated and purified by techniques well known in the art. For example, separation can be accomplished by precipitation, chromatography (e.g., column), phase separation (extraction) and distillation. The desired product can then be dried and purified by recrystallization.

The example that follows is intended to exemplify the claimed invention, and such example should not be construed as limiting the disclosure or the claimed invention.

EXAMPLE 1

All reactions described below were carried out under nitrogen. Chromatography was carried out using 230–400 mesh silica gel. The $^1H$ NMR spectra (300 or 400 MHz) were recorded in ppm and referred to $(CH_3)_4Si$ unless otherwise noted. All starting materials were purchased commercially and used without further purification, except the 4-benzyl-oxybenzaldehyde (Formula 37.0) which was recrystallized from toluene. The HPLC chiral assays of the hydroxy ester of Formula 34.0, the β-lactam of Formula 39.0, and the compound of Formula 11.0 were carried out on a Chiralcel ODH column (0.46 cm ID×25 cm) with a mobile phase of hexane:i-propanol (84:16) and a flow rate of 1.0 mL/min. For chemical purities a reversed phase HPLC was employed using μ-Bondapak Phenyl column (0.39 cm×30 cm) and $H_2O:CH_3CN$ (1:1) as a mobile phase. UV detectors at 225 nm were used for both of the above HPLC.

Step 1: Ethyl 4-hydroxycyclohexanecarboxylate (32.0)

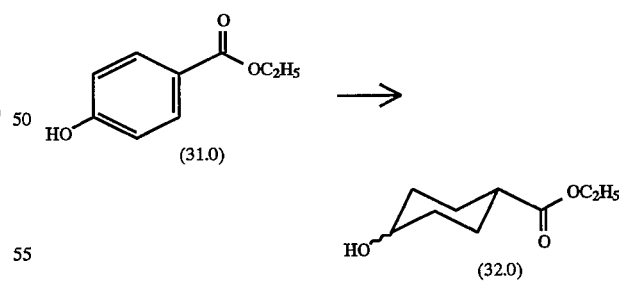

To a 1-L Pyrex pressure bottle were added sequentially 50 g of ethyl 4-hydroxybenzoate, 300 mL of methanol, and 5 g of 5% Rh on $Al_2O_3$. The sealed bottle was flashed with nitrogen and hydrogenated at 50 psi until $^1H$ NMR indicated complete reaction (about 8 to about 16 hrs). Filtration of the reaction mixture followed by concentration gave 50 g of the compound of Formula 32.0 as a mixture of trans and cis-isomers with a ratio of 78:22 as determined by GLC. The crude pale-yellow liquid was used directly in the oxidation step (Step 2 below) without further purification. HRMS:

173.1178 (MH⁺); calculated: 173.1171; ¹H NMR (CDCl₃) trans: 4.12 (q, J=7.2 Hz, 2H), 3.89 (m, 1H), 2.36 (m, 1H), 2.04–1.90 (m, 3H), 1.70–1.60 (m, 5H), 1.24 (t, J=7.2 Hz, 3H). IR: 1730 cm⁻¹.

Step 2: Ethyl 4-oxocyclohexanecarboxylate (33.0)

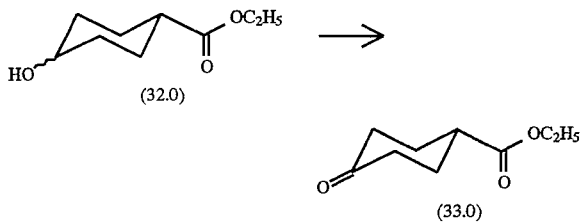

To a 3-L 3-neck flask equipped with a mechanical stirrer, a thermometer, and an addition funnel were added 50 g (292 mmol) of the compound of Formula 32.0 from Step 1, 33 mL (584 mmol) of acetic acid and 145 mL of commercial bleach (5.25% NaOCl). To the cooled reaction mixture, at 5° C., was added dropwise 479 mL of more bleach. The reaction was allowed to warm to room temperature for 1 hour and then was extracted with 3×400 mL ethyl acetate. The combined extract was washed with water, dried over MgSO₄, and concentrated to give 49 g of crude 33.0 as an oil which was used without purification. The spectrum data are identical to that of literature (see Sanchez, I. H.; Ortega, A.; Garcia, G.; Larraza, M. I.; Flores, H. J. Synthetic comm. 1985, 15, 141).

Step 3: Cyclicketal ester (2.2)

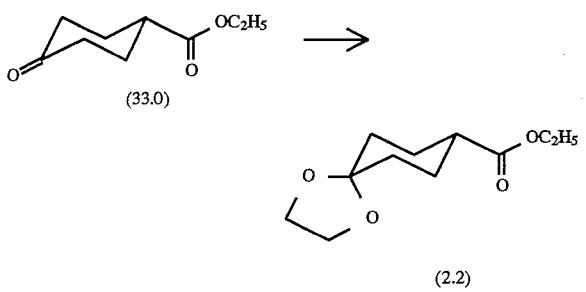

To a 2-L one-neck flask was added 307.5 g (1.968 mole) of the compound of Formula 33.0, 131.7 mL (2.362 mole) of ethylene glycol, and 3.74 g (19.68 mmol) of p-toluenesulfonic acid. With a distillation head attached, water produced was removed via an azotropical distillation. When the distillation slowed down, 75 mL of toluene was charged and the distillation was continued until about 4% starting material was left as determined by GLC. The cooled reaction was quenched portionwise into 450 mL ice cold saturated NaHCO₃ solution and extracted with 3×300 mL of ethyl acetate. The combined extract was washed with brine, dried with MgSO₄, and concentrated. The residue was distilled at 115° to 125° C./0.3 mmHg to give 319 g (81%) of the compound of Formula 2.2. HRMS: 215.1283 (MH⁺); calculated: 215.1292. ¹H NMR (CDCl₃) 4.13 (q, J=7.0 Hz, 2H), 3.96 (s, 4H), 2.4–2.3 (m, 1H), 2.0–1.9 (m, 2H), 1.9–1.75 (m, 4H), 1.65–1.5 (m, 2H), 1.26 (t, J=7.0 Hz, 3H). IR: 1730 cm⁻¹.

Step 4: Cyclicketal TMSenolether (3.2)

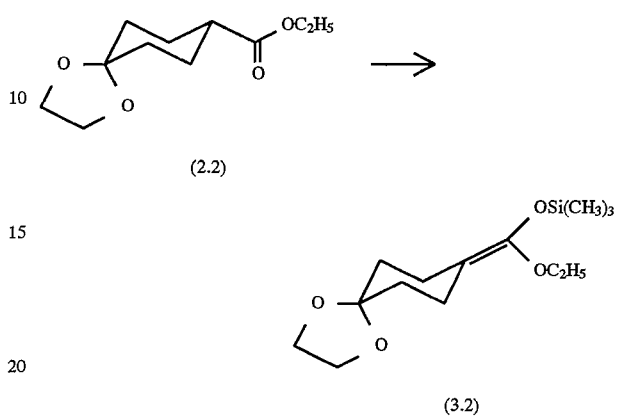

To a dry 1-L 3-neck flask equipped with a mechanical stirrer, an addition funnel, and a thermometer was added 130 mL of THF and 23.3 mL (166 mmol) of diisopropylamine. The mixture was cooled to –20° C. and 104 mL (166 mmol) of 1.6 M butyl lithium in hexane was added dropwise. After 30 minutes agitation at –20° C., a solution of 29.6 g (138 mmol) of the compound of Formula 2.2 in 30 mL of THF was added dropwise and the resulting mixture was stirred at –20° C. for 1 hour. To the enolate formed, at –20° C., was added dropwise 26.3 mL (207 retool) of (CH₃)₃SiCl (TMSCl). The mixture was stirred at –20° C. for 30 minutes and then allowed to warm to room temperature for 1 hour. The THF was distilled off and the residue was transferred into a smaller flask via a Schlenk air-free filter. High vacuum distillation at 87°–92° C./0.3 mmHg produced 38.9 g (94%) of the compound of Formula 3.2. HRMS: 285.1522 (MH⁺); calculated: 285.1512. ¹H NMR (CDCl₃) 3.89 (s, 4H), 3.71 (q, J=7.0 Hz, 2H),2.25–2.20 (m, 2H), 2.19–2.10 (m, 2H), 1.48–1.40 (m, 4H), 1.15 (t, J-7.0 Hz, 3H), 0.13 (s, 9H).

Step 5: Hydroxy ester (34.0)

(A) N-(2-naphthalenesulfonyl) D-valine (18.1)

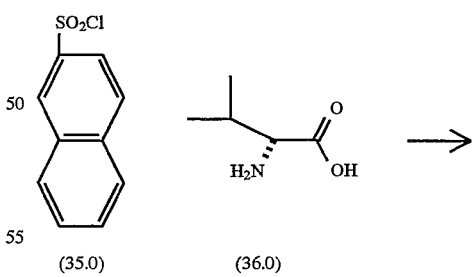

-continued

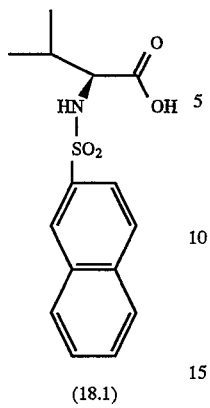

(18.1)

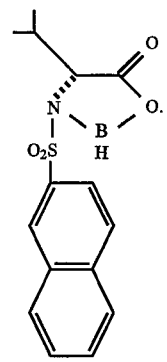

(24.0)

To a 12-L 3-neck flask with a mechanical stirrer, an addition funnel, and a thermometer were added 400 g (3.414 mol) of D-valine (36.0), 3 L of water, 380 mL of THF, and 1190 mL (8.572 mol) of triethylamine (TEA). To this solution was added dropwise at 5°–10° C. a solution of 774 g (3.414 mol) of 2-naphthalenesulfonyl chloride (35.0) in 800 mL THF. The mixture was allowed to warm to room temperature and stirred for 2 hours. Evaporation of THF followed by quenching into 4 L of 3 N HCl precipitated crude product. Crystallization of the crude product from t-butyl methyl ether gave 910 g (87%) of 18.1. M.p: 170°–172° C. (literature gives the m.p. as 170°–172° C.-see Kiyooka, S.; Kaneko, Y.; Komura, M.; Matsuo, H.; Nakano, M. J. Org. Chem., 1991, 56, 2276.). The spectrum data are identical to that of the literature.

(B) Hydroxy Ester (34.0) formation

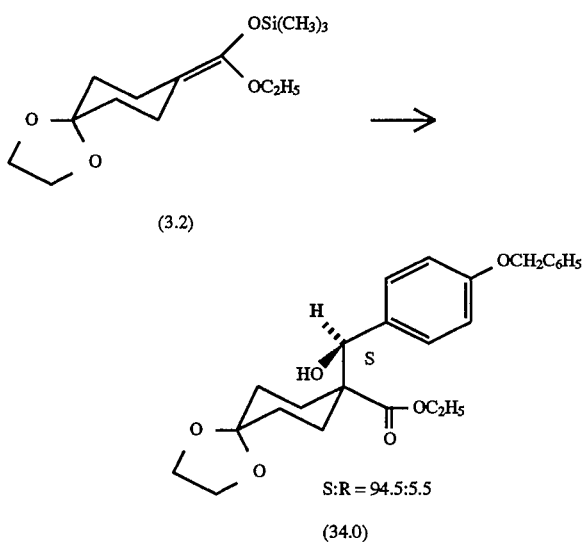

To a dry 50 mL 2-neck flask with a magnetic stirrer and thermometer were added 1.23 g (4.0 retool) of N-(2-naphthalenesulfonyl) D-valine (18.1) and 5 mL of propionitrile (dried over 3Å molecular sieves). To the cooled mixture at 5° C. was added dropwise 4.0 mL (4.0 mmol) of 1.0M BH₃.THF to produce in situ the chiral catalyst:

The resulting mixture was cooled to −78° C. and 3.15 g (11 mmol) of the TMSenol ether (Formula 3.2) was added dropwise. To the resulting mixture was added dropwise, in 2 hours using a syringe pump, a solution of 2.12 g (10 retool) 4-benzyloxybenzaldehyde (37.0)

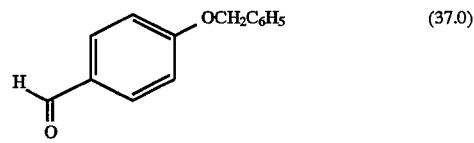

(37.0)

in 4 mL propionitrile. After stirring at −78° C. for another hour, the reaction was quenched into 50 mL of ice cold saturated NaHCO₃ and extracted with 3×50 mL of ethyl acetate. The combined extract was washed with NaHCO₃ 4 times to remove any catalyst, dried over MgSO₄, and concentrated to a small volume. The residue was redissolved in a small amount of THF (about 4 ml) and 0.7 equivalents of 1.0M (C₄H₉)₄NF in THF was added dropwise to remove the trimethylsilyl (TMS) group. Concentration of the THF was followed by quenching into brine. The product was extracted with toluene, washed with brine, dried over MgSO₄, and concentrated to a small volume. Crystallization gave 3.21 g (75%) of the compound of Formula 34.0 with an 89% e.e. (enantiomer excess). M.p: 83°–85° C. HRMS: 449.1940 (MNa⁺); calculated: 449.1942. ¹H NMR (CDCl₃) 7.40–7.25 (m, 5H), 7.07 (d, J=8.7 Hz, 2H), 6.85 (d, J=8.7 Hz, 2H),4.99 (s, 2H), 4.56 (d, J=5.6 Hz, 1H), 4.15–4.0 (m, 2H), 3.85 (s, 4H), 2.80 (d, J=5.6 Hz, 1H), 2.3–2.2 (m, 1H), 2.0–1.9 (m, 1H), 1.7–1.4 (m, 6H), 1.14 (t, J=7.1 Hz, 3H). IR: 1720 cm⁻¹.

Step 6: Hydroxy amide (38.0)

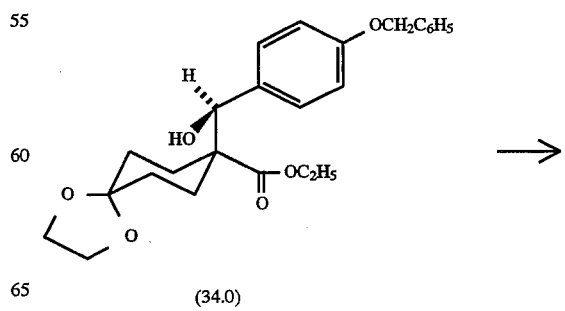

(34.0)

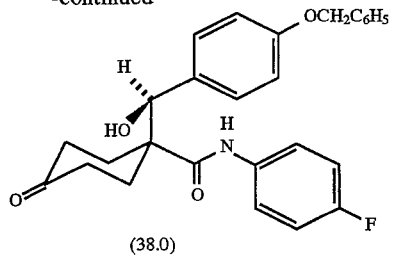

(38.0)

To a dry 2-L 3-neck flask with a mechanical stirrer, an addition funnel, and a thermometer was added 41.3 mL (436 mmol) of 4-fluoro-aniline and 120 mL of $CH_2Cl_2$. To the mixture was added 218 mL (436 mmol) of 2.0M $(CH_3)3Al$ in hexane. After agitation at room temperature for 30 minutes, a solution of 46.7 g (109 mmol) of hydroxy ester (34.0) in 110 mL of $CH_2Cl_2$ was added dropwise and the resulting mixture was heated at 50° to 55° C. for 2 days. The cooled reaction was quenched dropwise into a mixture of 700 mL of 3N HCl and 400 mL of toluene and extracted with 2×400 mL of ethyl acetate. The combined ethyl acetate extract was washed with 2×300 mL of 3N HCl, 300 mL brine, and concentrated. The residue was redissolved in 250 mL of THF and then hydrolyzed at room temperature for 3 days with the addition of 300 mL of 3 N HCl. After removal of the THF, the crude product was filtered and slurried with saturated $NaHCO_3$ to give 40.9 g (38.0) which was used for the cyclization (Step 7 below) without purification. An analytical sample was recrystallized from ethyl acetate/hexane. M.p: 173°–175° C. HRMS: 448.1924 (MH$^+$); calculated: 448.1920. $^1$H NMR (CDCl$_3$) 8.88 (s, 1H), 7.48 (dd, J=8.9, 4.8 Hz, 2H), 7.40–7.30 (m, 5H), 7.13 (d, J=8.6 Hz, 2H), 7.04 (t, J=8.6 Hz, 2H), 6.87 (d, J=8.6 Hz, 2H), 5.00 (s, 2H), 4.56 (s, 1H), 3.16 (bs, 1H), 2.85–2.75 (m, 1H), 2.75–2.65 (m, 1H), 2.45–2.32 (m, 2H), 2.27 (dm, J=15.8 Hz, 1H), 2.15–2.05 (m, 1H), 1.93 (td, J=13.4, 5.3 Hz, 1H), 1.55 (td, J=13.4, 5.3 Hz, 1H). IR: 1700, 1640 cm$^{-1}$.

Step 7: Ketone β-Lactam (39.0)

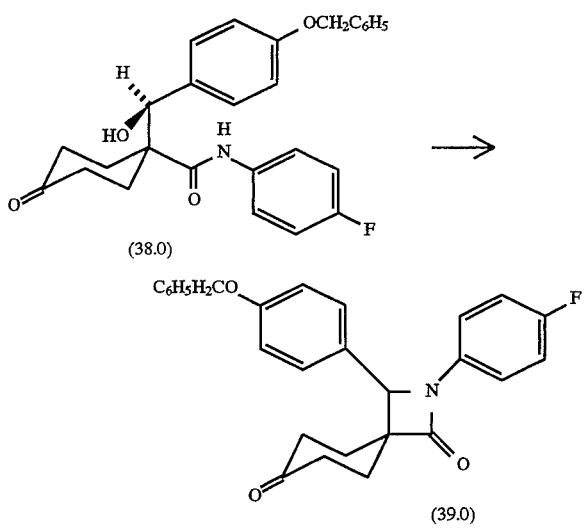

To a 2-L 3-neck flask with a mechanical stirrer, an addition funnel, and a thermometer were added 39.3 g of the crude hydroxy amide (38.0), 1.0 liter of $CH_2Cl_2$ and 4 g of $C_6H_5CH_2N(C_2H_5)_3Cl$. To the mixture was added slowly through the addition funnel 232 g of 50% NaOH and 19 mL (132 mmol) of $(C_2H_5O)_2P(O)Cl$ in 20 minutes. The resulting mixture was stirred at room temperature for 2 hours, then quenched slowly into 2 L of ice cold 3N HCl with agitation, and then extracted with 3×500 mL of ethyl acetate. The combined extract was washed with brine, dried over $MgSO_4$, and concentrated. Addition of 200 mL of $(C_2H_5)_2O$ to the residue precipitated 23.4 g (59% over two steps) of the compound of Formula 39.0. The enantiomer excess was determined to be 99.8%. M.p: 127°–129° C. HRMS: 430.1818 (MH$^+$); calcd: 430.1805. $^1$H NMR (CDCl$_3$) 7.34–7.17 (m, 7H), 7.09 (d, J=8.6 Hz, 2H), 6.90–6.96 (m, 4H), 4.95 (s, 2H), 4.80 (s, 1H), 2.80–2.75 (m, 1H), 2.5–2.45 (m, 3H), 2.25–2.15 (m, 1H), 1.95–1.80 (m, 2H), 1.52–1.42 (m, 1H). IR: 1735, 1720 cm$^{-1}$.

Step 8: Hydroxy β-lactam (40.0)

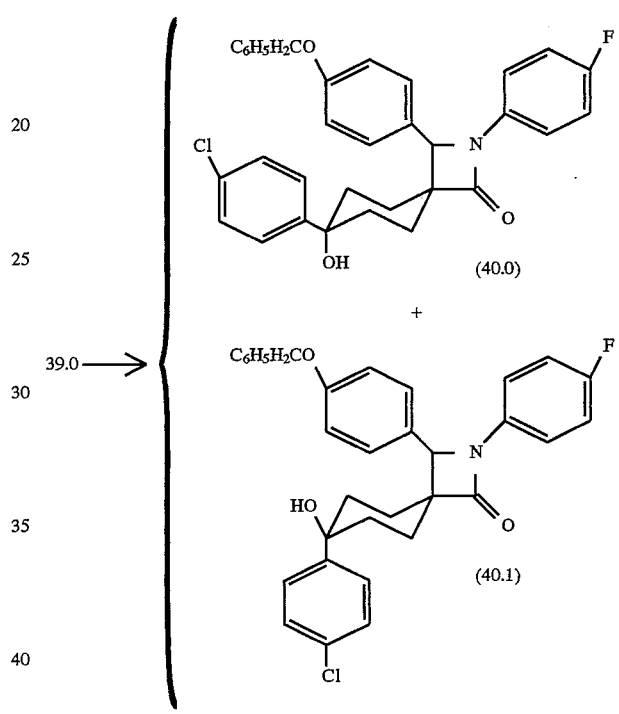

To a dry 12-L 3-neck flask with a mechanical stirrer, an addition funnel, and a thermometer was added 1750 mL of 1.0M 4-ClC$_6$H$_4$MgBr. The mixture was heated to 48° to 52° C. and a solution of 500 g (1.164 mmol) of the compound of Formula 39.0 in 2 L toluene was added dropwise in 1 hour. The resulting mixture was stirred for another 30 minutes at the same temperature, cooled to room temperature, quenched slowly into 6 L ice cold 3N HCl, and extracted with 3×3 L of ethyl acetate. The combined extract was washed with 2×3 L of 3N HCl and brine, dried over $MgSO_4$, and concentrated to give 567 g of crude product as a mixture of two diastereomers 40.0 and 40.1 (ratio 94:6 of 40.0 to 40.1). The crude mixture was used directly in hydrogenation Step 9 below. HRMS: 541.1820 (M$^+$); calculated 541.1816. $^1$H NMR (CDCl$_3$, major isomer only) 7.50–7.20 (m, 8H), 7.00 (d, J=8.6 Hz, 2H), 6.93 (t, J=8.6 Hz, 2H), 5.04 (s, 2H), 4.86 (s, 1H), 2.60–2.50 (m, 1H), 2.16 (td, J=13.8, 4.3 Hz, 1H), 2.05–1.90 (m, 3H), 1.63 (rim, J=13.8 Hz, 1H), 1.32 (dm, J=14.3 Hz, 1H), 1.10 (td, J=13,8, 4.3 Hz, 1H). IR: 1730 cm$^{-1}$.

Step 9: Hydrogenation to produce Formula 11.0

40.1 + 40.0 ⟶
(mixture)

-continued

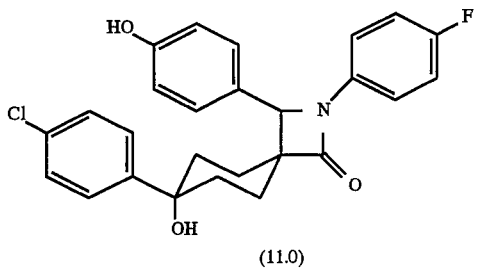

(11.0)

To a 2-L Pyrex pressure bottle were charged 35 g of 10% Pd/C, 350 g (about 645 mmol) of the crude mixture of 40.0 and 40.1, and 145 g (645 mmol) of $ZnBr_2$. The bottle was sealed with a rubber septum, evacuated, and flashed with nitrogen 3 times. To the sealed bottle was added through a cannula 1100 mL of ethanol. The mixture was hydrogenated at 50 to 55 psi for 16 hours at ambient temperature, filtered through a pad of celite, and concentrated. The palladium was covered with sand. The residue was redissolved in 1 L of ethyl acetate, quenched slowly into 1 L of ice cold saturated $NaHCO_3$, and extracted with 2×300 mL of ethyl acetate. The combined extract was washed with saturated $NH_4Cl$ and brine, dried over $MgSO_4$, and concentrated. Addition of 1 L of $CH_2Cl_2$ precipitated 178 g (63% over 2 steps) of the compound of Formula 11.0. M.p: 235°–236° C. Elemental analysis: C, 69.16; H, 5.42; N, 3.19; Cl, 7.75; F, 4.30. calculated for $C_{26}H_{23}ClFNO_3$: C, 69.10; H, 5.13; N, 3.10; Cl, 7.86; F, 4.21. $[\alpha]^{25} = +50.9$ (8.33 mg/2 mL $CH_3OH$). Chiral HPLC: 99.9% e.e. $^1H$ NMR (DMSO-$d_6$) 9.57 (s, 1H), 7.40–7.15 (m, 10H), 6.80 (d, J=8.5 Hz, 2H), 5.14 (s, 1H), 5.04 (s, 1H), 2.30 (td, J=12.8, 3.5 Hz, 1H), 2.05 (td, J=13.6 Hz, 3.5 Hz, 1H), 1.96 (td, J=13.6, 3.9 Hz, 1H), 1.87 (rim, J=13.6 Hz, 1H), 1.72 (rim, J=13.6 Hz, 1H), 1.48 (dm, J=13.6 Hz, 1H), 1.13 (din, J=12.8 Hz, 1H), 0.84 (td, J=13.6, 3.5 Hz, 1H). $^{13}C$ NMR (DMSO-$d_6$, ppm) 170.6, 158.1 (d, J=240 Hz), 157.4, 149.4, 134.1 (d, J=2.3 Hz), 130.9, 130.0, 126.6, 125.4, 118.6 (d, J=8.0 Hz), 116.0 (d, J=23 Hz),115.6, 70.2, 64.9, 58.5, 34.8, 33.4, 27.5, 21.7. IR: 1730 cm$^{-1}$.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for producing a compound of the formula:

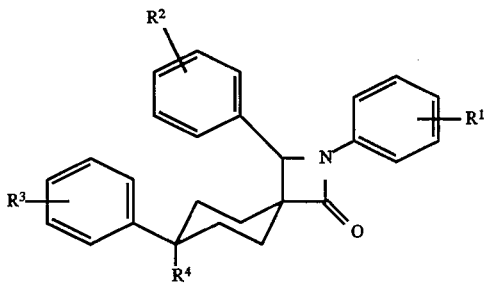

(1.0)

wherein:

$R^1$, $R^2$ and $R^3$ are each independently selected from the group consisting of:
(a) H;
(b) halo;
(c) —$OR^5$ wherein $R^5$ is: H, $C_1$ to $C_6$ alkyl, aryl, aralkyl, alkaryl, heteroaryl, $C_2$ to $C_6$ alkenyl, $C_2$ to $C_6$ alkynyl, $C_3$ to $C_7$ cycloalkyl, $C_3$ to $C_7$ cycloalkenyl, or —C(O)$R^6$ wherein $R^6$ is $C_1$ to $C_6$ alkyl, aryl, or —$OR^7$ wherein $R^7$ is $C_1$ to $C_6$ alkyl or aryl; and (d) —C(O)$R^8$ wherein $R^8$ is $C_1$ to $C_6$ alkyl, aryl, heteroaryl, aralkyl, cycloalkyl, —$OR^9$ (wherein $R^9$ is $C_1$ to $C_6$ alkyl or aryl), or —$N(R^{10})_2$ (wherein each $R^{10}$ is independently selected from the group consisting of H, $C_1$ to $C_6$ alkyl and aryl);

$R^4$ is H or —OH;

said process comprising:

(a) reacting, under an inert atmosphere, in a suitable organic solvent, a compound of formula:

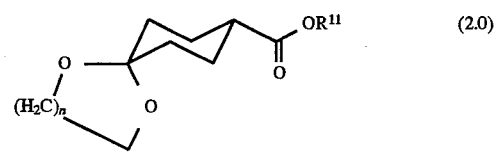

(2.0)

with an enolization base and a silylation reagent to produce a compound of the formula:

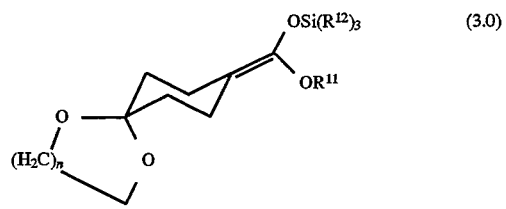

(3.0)

wherein n is 1 or 2, $R^{11}$ is a $C_1$ to $C_4$ alkyl group, $R^{12}$ is a $C_1$ to $C_4$ alkyl group;

(b) reacting, under an inert atmosphere, in a suitable organic solvent, the compound of Formula 3.0 with a chiral catalyst and a compound of the formula:

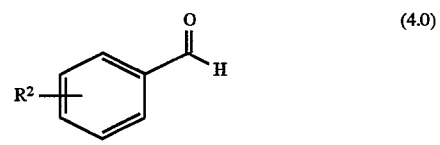

(4.0)

wherein $R^2$ is defined above, with the proviso that $R^2$ is not OH, and then reacting the resulting product with a deprotecting reagent to remove the —$Si(R^{12})_3$ protecting group thereby forming a compound of the formula:

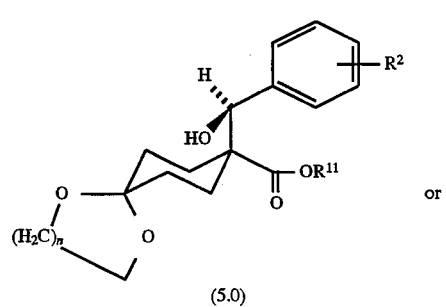

(5.0)

or

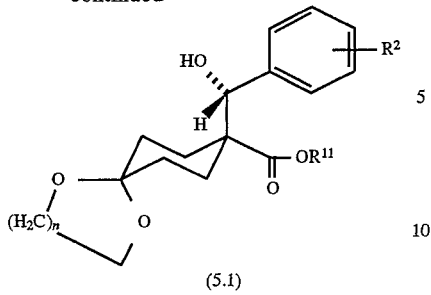

(5.1)

or an enantiomeric mixture of 5.0 and 5.1; said chiral catalyst being a complex formed from borane and a compound of the formula:

(6.0)

wherein $R^{13}$ is aryl or fused aryl, and $R^{14}$ is

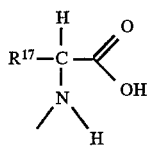

wherein $R^{17}$ is —CH(CH$_3$)$_2$, —C(CH$_3$)$_3$, phenyl, benzyl or

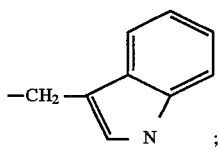

;

(c) reacting a compound of Formula 5.0 or 5.1 or an enantiomeric mixture of 5.0 or 5.1, in a suitable organic solvent, with a compound of the formula:

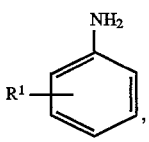

(7.0)

wherein $R^1$ is as defined above, with the proviso that $R^1$ is not OH, with a Lewis acid and with a strong acid, to produce a compound of the formula:

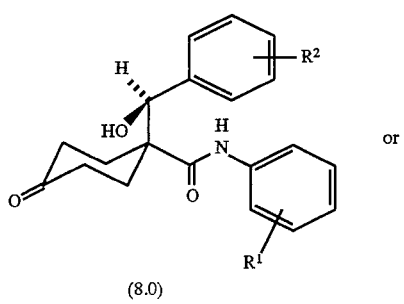

(8.0)

or

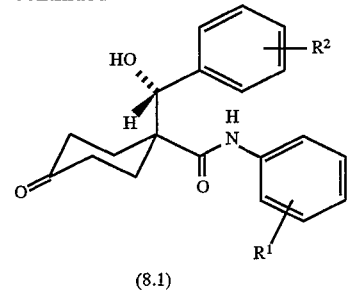

(8.1)

or an enantiomeric mixture of 8.0 or 8.1;

(d) reacting a compound of Formula 8.0 or 8.1 or an enantiomeric mixture of 8.0 and 8.1, in a suitable solvent, with a reagent that converts hydroxy groups into leaving groups, with a strong base, and with a phase transfer catalyst, to produce a compound of the formula:

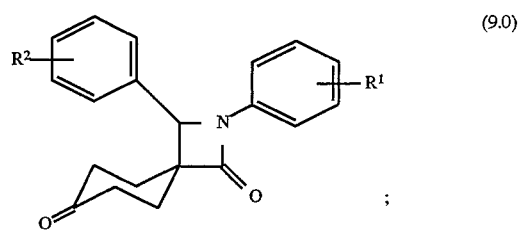

(9.0)

;

(e) reacting a compound of Formula 9.0, in a suitable solvent, with a compound of the formula:

(10.0)

wherein $R^3$ is as defined above, with the proviso that $R^3$ is not OH, to produce a compound of the formula:

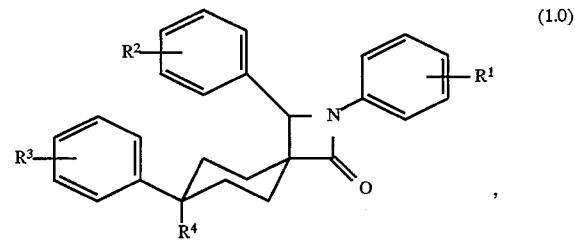

(1.0)

wherein $R^4$ is a hydroxy group;
with the proviso that $R^1$, $R^2$ and $R^3$ are not —OH;

(f) when $R^1$, $R^2$, and/or $R^3$ in Formula 1.0 in (e) above is —OR$^5$, wherein $R^5$ is aralkyl, optionally hydrogenating said compound of Formula 1.0 in an appropriate alkanol solvent with a hydrogenation catalyst and a Lewis acid selected from the group consisting of MgX$_2$, TiX$_4$, and ZnX$_2$, wherein X is Cl or Br, thereby converting said —OR$^5$ to —OH; and (g) optionally converting said —OH $R^4$ substituent to H by heating a compound of Formula 1.0 (wherein $R^4$ is —OH) with an acid to produce a dehydrated compound of Formula 1.2:

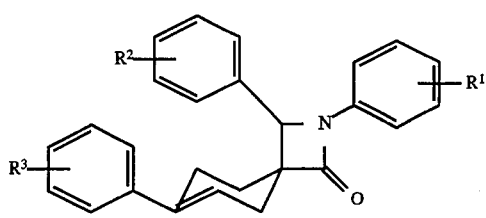

(1.2)

and then hydrogenating the compound of Formula 1.2 in a $C_1$ to $C_6$ alkanol solvent using a hydrogenation catalyst to produce a compound of Formula 1.0 wherein $R^4$ is H.

2. The process of claim 1 wherein $R^1$, $R^2$ and $R^3$ are: independently selected from H, halo or —$OR^5$ wherein $R^5$ is selected from H, $C_1$ to $C_6$ alkyl, or aralkyl.

3. A process for producing a compound of the formula:

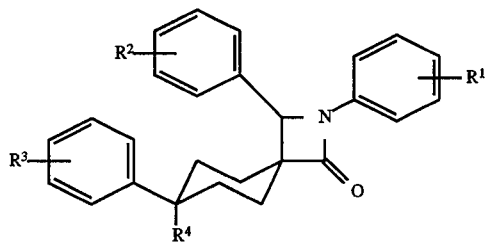

(1.0)

wherein $R^1$, $R^2$ and $R^3$ are each independently selected from the group consisting of:

(a) H:

(b) halo:

(c) —$OR^5$ wherein $R^5$ is: H, $C_1$ to $C_6$ alkyl, aryl, aralkyl, alkaryl, heteroaryl, $C_2$ to $C_6$ alkenyl, $C_2$ to $C_6$ alkynyl, $C_3$ to $C_7$ cycloalkyl, $C_3$ to $C_7$ cycloalkenyl, or —C(O)$R^6$ wherein $R^6$ is $C_1$ to $C_6$ alkyl, aryl, or —$OR^7$ wherein $R^7$ is $C_1$ to $C_6$ alkyl or aryl; and (d) —C(O)$R^8$ wherein $R^8$ is $C_1$ to $C_6$ alkyl, aryl, heteroaryl, aralkyl, cycloalkyl, —$OR^9$ (wherein $R^9$ is $C_1$ to $C_6$ alkyl or aryl), or —N($R^{10}$)$_2$ wherein each $R^{10}$ is independently selected from H, $C_1$ to $C_6$ alkyl and aryl;

$R^4$ is —OH;

and wherein at least one of $R^1$, $R^2$ and $R^3$ is OH in the final product of formula 1.0;

said process comprising: hydrogenating a compound of Formula 1.0, wherein at least one of $R^1$, $R^2$ and $R^3$ corresponding to the —OH group in the final product is —$OR^5$ wherein $R^5$ is aralkyl, in an a suitable alkanol solvent, with a hydrogenation catalyst and a Lewis acid selected from the group consisting of $MgX_2$, $TiX_4$, and $ZnX_2$, wherein X is Cl or Br, thereby converting said —$OR_5$ to —OH.

4. The process of claim 1 wherein $R^1$ is selected from H, Cl, F or —$OCH_3$; $R^2$ is selected from H, —OH, benzyloxy, 4-chlorobenzyloxy, 4-nitrobenzyloxy, 4-methoxybenzyloxy or —$OCH_3$; and $R^3$ is selected from H, Cl, F or —$OCH_3$.

5. The process of claim 1 wherein a compound of formula:

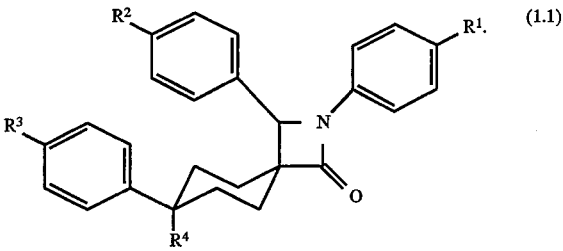

(1.1)

is produced.

6. The process of claim 1 wherein said enolization base is selected from: KO-t-$C_4H_9$, $NaH_2$, sec-butyl lithium, t-butyl lithium, lithium bis(trimethylsilyl)amide, and LiN($R^{15}$)$_2$ wherein each $R^{15}$ is independently a $C_1$ to $C_6$ alkyl; said silylation reagent is a compound of the formula ($R^{12}$)$_3$Si$R^{16}$ wherein $R^{12}$ is selected from methyl, ethyl or t-butyl, and $R^{16}$ is selected from Cl, Br, or I; said $R^{13}$ is selected from 2-naphthyl, 4-nitrophenyl, 4-methylphenyl, or 2,4,6-trimethylphenyl; and said $R^{14}$ is

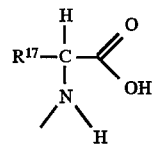

wherein $R^{17}$ is —CH($CH_3$)$_2$, —C($CH_3$)$_3$, phenyl, benzyl or

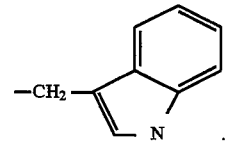

7. The process of claim 6 wherein said enolization base is Li(i-$C_3H_7$)$_2$ and said silylation reagent is ($CH_3$)$_3$SiCl.

8. A process for producing a compound of the formula:

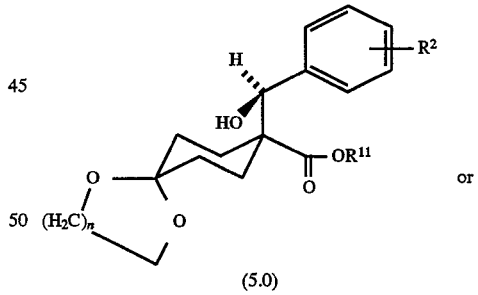

(5.0)

or

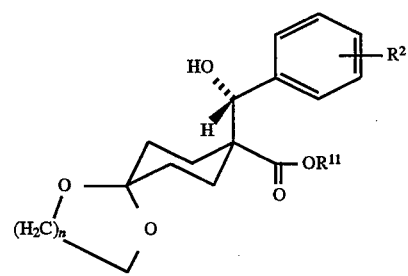

(5.1)

(or an enantiomeric mixture of 5.0 and 5.1) wherein;

$R^2$ is selected from the group consisting of:

(a) H;

(b) halo;

(c) —OR⁵ wherein R⁵ is: $C_1$ to $C_6$ alkyl, aryl, aralkyl, alkaryl, heteroaryl, $C_2$ to $C_6$ alkenyl, $C_2$ to $C_6$ alkynyl, $C_3$ to $C_7$ cycloalkyl, $C_3$ to $C_7$ cycloalkenyl, or —C(O)R⁶ wherein R⁶ is $C_1$ to $C_6$ alkyl, aryl, or —OR⁷ wherein R⁷ is $C_1$ to $C_6$ alkyl or aryl; and (d) —C(O)R⁸ wherein R⁸ is $C_1$ to $C_6$ alkyl, aryl, heteroaryl, aralkyl, cycloalkyl, —OR⁹ (wherein R⁹ is $C_1$ to $C_6$ alkyl or aryl), or —N(R¹⁰)₂ wherein each R¹⁰ is independently selected from H, $C_1$ to $C_6$ alkyl and aryl;

n is 1 or 2; and

R¹¹ is a $C_1$ to $C_4$ alkyl group;

by reacting, in a suitable organic solvent, the compound of Formula 3.0

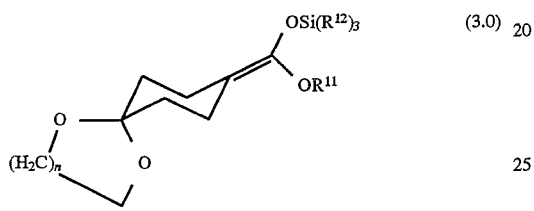

(3.0)

wherein R¹² is a $C_1$ to $C_4$ alkyl group, and n and R¹¹ are as defined above, with a chiral catalyst and a compound of the formula:

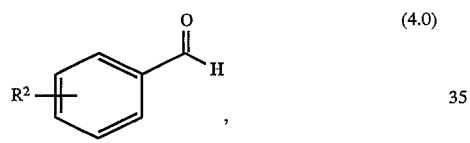

(4.0)

with the proviso that R² is not OH;

and then reacting the resulting product with a deprotecting reagent to remove the —Si(R¹²)₃ protecting group;

said chiral catalyst being a complex formed from borane and a compound of the formula:

```
    R¹⁴
    |
    SO₂
    |
    R¹³
```
(6.0)

wherein R¹³ is aryl or fused aryl, and R¹⁴ is

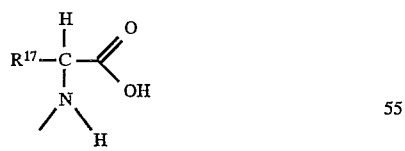

wherein R¹⁷ is —CH(CH₃)₂, —C(CH₃)₃, phenyl, benzyl or

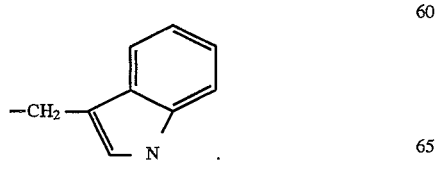

9. The process of claim 6 wherein the chiral catalyst is:

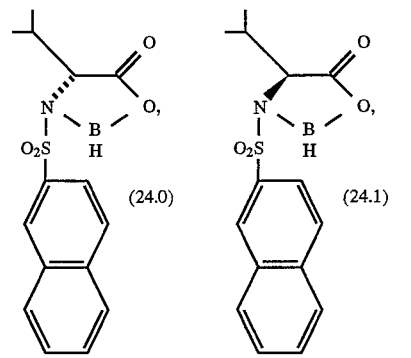

(24.0)  (24.1)

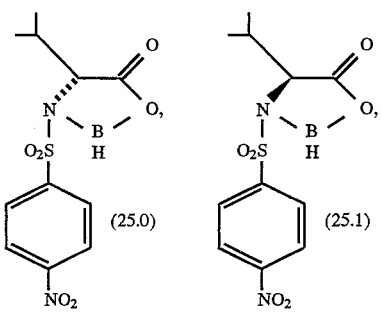

(25.0)  (25.1)

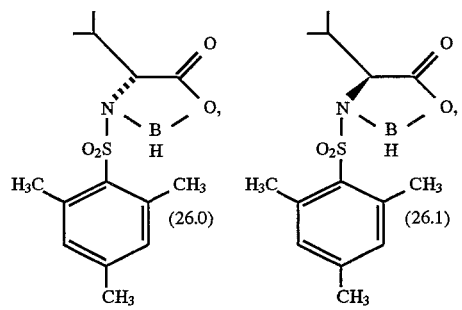

(26.0)  (26.1)

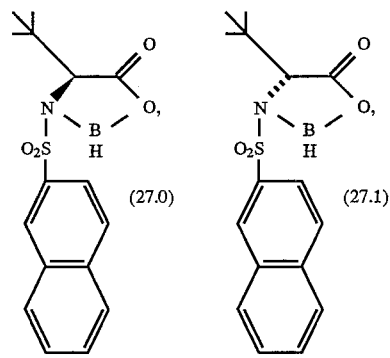

(27.0)  (27.1)

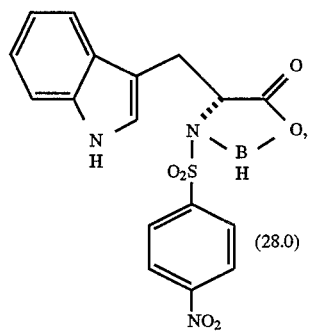

(28.0)

-continued

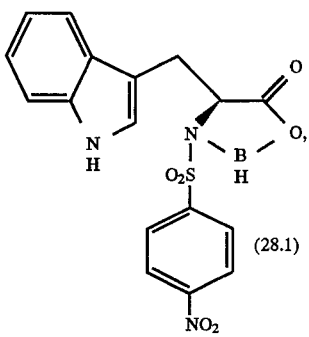

(28.1)

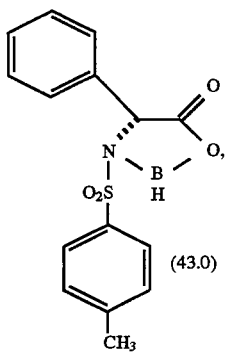

(43.0)

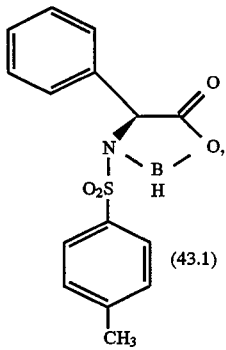

(43.1)

a mixture of 24.0 and 24.1, a mixture of 25.0 and 25.1, a mixture of 26.0 and 26.1, a mixture of 27.0 and 27.1, a mixture of 28.0 and 28.1 or a mixture of 43.0 and 43.1.

10. The process of claim 9 wherein said chiral catalyst is selected from 24.0, 24.1 or mixtures thereof.

11. The process of claim 1 wherein said Lewis Acid used in Step (c) is selected from $(CH_3)_3Al$, $(C_2H_5)_3Al$ or $Cl_3Al$; and said strong acid is selected from HCl, $H_2SO_4$ or $CF_3CO_2H$.

12. The process of claim 11 wherein said Lewis Acid is $(CH_3)_3Al$; and said strong acid is aqueous HCl.

13. The process of claim 1 wherein said reagent that converts a hydroxy group into a leaving group is selected from $(C_2H_5O)_2P(O)Cl$, 2,4,6-trichlorobenzoyl chloride, or 2,6-dichlorobenzoyl chloride; said base is selected from NaOH, $NaOCH_3$, KOH, $KOCH_3$, or $KO$-$t$-$C_4H_9$; and said phase transfer catalyst is selected from $C_6H_5CH_2N(C_2H_5)_3Cl$, $C_6H_5CH_2N(C_2H_5)_3Br$, tetrabutyl-ammonium sulfate, tetrabutylammonium acetate, tetrabutylammonium chloride, tetrabutylammonium iodide, benzyltributylphosphorous chloride, tetrabutylammonium hydroxide, or tetraphenylphosphorous iodide.

14. The process of claim 13 wherein said reagent that converts a hydroxy group into a leaving group is $(C_2H_5O)_2P(O)Cl$; said base is NaOH; and said phase transfer catalyst is $C_6H_5CH_2N(C_2H_5)_3Cl$.

15. The process of claim 1 wherein one of $R^1$, $R^2$ or $R^3$ is a protected hydroxy group and at least one of the remaining $R^1$, $R^2$ and $R^3$ substituents is halo, end Step (f) is conducted, and said hydrogenation catalyst is selected from Pd/C, Pt/C, Ni/C or Raney Nickel. :

16. The process of claim 15 wherein one of $R^1$, $R^2$ or $R^3$ is selected from benzyloxy, 4-methoxybenzyloxy, 4-chlorobenzyloxy or 4-nitrobenzyloxy; and the remaining $R^1$, $R^2$ and $R^3$ substituents are independently selected from Cl, F or H.

17. The process of claim 16 wherein the Lewis acid in Step (f) is $ZnBr_2$; the alkanol solvent is ethanol; and one of $R^1$, $R^2$ or $R^3$ is benzyloxy.

18. The process of claim 17 wherein $R^2$ is benzyloxy; $R^3$ is Cl; $R^1$ is H or F; and $R^4$ is —OH.

19. The process of claim 3 wherein at least one of the remaining $R^1$, $R^2$ and $R^3$ is halo.

20. The process of claim 1 for the preparation of a compound of formula 1.0 having the formula 11.0;

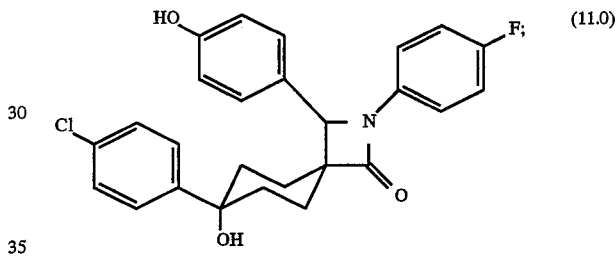

wherein:

(a) said compound of formula 2.0 is a compound of formula 2.2:

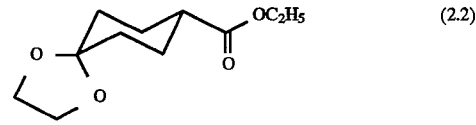

and said compound of 3.0 is a compound of formula 3.2:

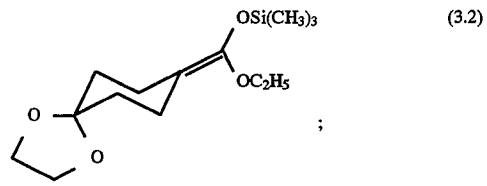

(b) said compound of formula 4.0 is a compound of formula 37.0:

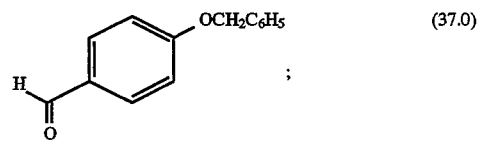

said chiral catalyst is a compound of formula 24.0:

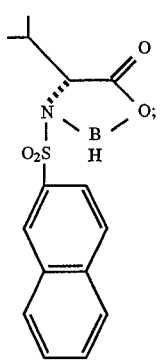
(24.0)

and said compound of 5.0 is a compound of 34.0.:

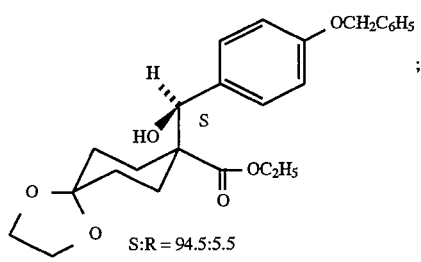
(34.0)

S:R = 94.5:5.5

(c) said compound of formula 7.0 is 4-fluoroaniline; and said compound of formula 8.0 is a compound of formula 38.0:

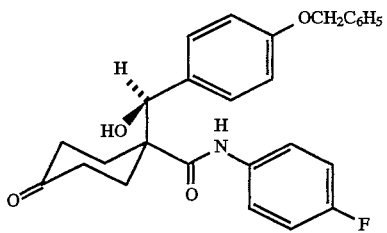
(38.0)

(d) said compound of formula 9.0 is a compound of formula 39.0:

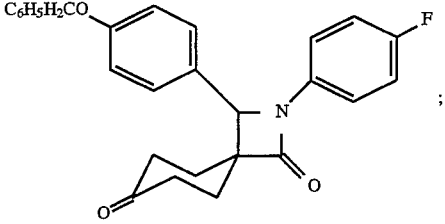
(39.0)

(e) said compound of formula 10.0 is 4-ClC$_6$H$_4$MgBr; and said compound of formula 1.0 is a mixture of compounds of formulas 40.0 and 40.1:

(40.0)

(40.1)

and (f) said mixture of compounds of formulas 40.0 and 40.1 is hydrogenated.

* * * * *